United States Patent [19]
Cappello et al.

[11] Patent Number: 5,496,712
[45] Date of Patent: Mar. 5, 1996

[54] HIGH MOLECULAR WEIGHT COLLAGEN-LIKE PROTEIN POLYMERS

[75] Inventors: Joseph Cappello, San Diego; Franco A. Ferrari, La Jolla, both of Calif.

[73] Assignee: Protein Polymer, San Diego, Calif.

[21] Appl. No.: 972,032

[22] Filed: Nov. 5, 1992

Related U.S. Application Data

[63] Continuation-in-part of Ser. No. 791,960, Nov. 12, 1991, abandoned, which is a continuation-in-part of Ser. No. 609,716, Nov. 6, 1990.

[51] Int. Cl.$^6$ ............ C12P 21/02; C12N 15/12; C07K 14/245; C07K 14/47
[52] U.S. Cl. ............ 435/69.1; 435/252.33; 536/23.5; 530/356; 530/388.9; 530/389.8
[58] Field of Search ............ 435/69.1, 252.33; 536/23.5; 530/354, 356, 388.9, 389.8

[56] References Cited

FOREIGN PATENT DOCUMENTS

| | | |
|---|---|---|
| 8803533 | 11/1986 | WIPO. |
| 8805082 | 12/1987 | WIPO. |
| 9005177 | 11/1988 | WIPO. |

OTHER PUBLICATIONS

I. Goldberg, et al. (1989) Gene 80:305–314. Cloning and expression of a collagen–analog–encoding synthetic gene in *E. coli.*
T. Kempe, et al. (1985) Gene 39:239–245. Multiple copy genes: production and modification of monomeric peptides from large multimeric fusion proteins.
M. Lennick, et al. (1987) Gene 61:103–112. High-level expression of a–human atrial natriuretic peptide from multiple joined genes in *E. coli.*
W. Taylor and P. Hagerman (1987) Gene 53:139–144. A general method for cloning DNA fragments in multiple copies.
L. Aslund, et al. (1987) Proc. Natl. Acad. Sci., USA 84:1399–1403. Synthetic gene contruct expressing a repeated and highly immunogenic epitope of the *P. falciparum* antigen Pf1155.
M. Schulz, et al. (1987) J. Bact. 169:5385–5392. Increased expression in *E. coli* of a synthetic gene encoding human somatomedin C after gene duplication and fusion.
S. Kim and W. Szybalski (1988) Gene 7:1–8. Amplifiation of cloned DNA as tandem multimers using BspM1–generated asymmetric cohesive ends.
S. Takeshita, et al. (1988) Gene 71:9–18. Tandem gene amplification in vitro for rapid and efficient expression in animal cells.
G. Bressan, et al. (1987) Biochemistry 26:1497–1503. Repeating structure of chick tropoelastin revealed by complementary DNA cloning.
S. Shen (1984) Proc. Natl. Acad. Sci., USA 81:4627–4631. Multiple joined genes prevent product degradation in *E. coli.*
M. Doel, et al. (1980) Nuc. Acids Res. 8:4575–4592. The expression in *E. coli* of synthetic repeating polymeric genes coding for poly)L–aspartyl–L–phenylalanine).
J. Hartley, et al. (1981) Gene 13:347–353. Cloning multiple copies of a DNA segment.
J. Sadler, et al. (1980) Gene 8:279–300. Plasmids containing many tandem copies of a synthetic lactose operator.
Miller, E. J. (1985) Ann. N.Y. Acad. Sci. 460, 1–13.
Fleishmajer, et al. Collagen fibrillogenesis in human skin. *Annals of the New York Academy of Sciences* 260:246–257 (1985).

*Primary Examiner*—Charles L. Patterson, Jr.
*Attorney, Agent, or Firm*—Bertram I. Rowland

[57] ABSTRACT

Collagen-like polymers having repetitive triads are produced having reduced proline content, where glycine is the initial amino acid and the subsequent amino acids are varied, while retaining at least a minimum percentage of prolines. The resulting polymers have collagen-like properties, but are capable of being produced in unicellular microorganisms at high molecular weights and in high efficiency. The polymers while retaining collagen-like characteristics, include various novel sequences which impart new characteristics, finding wide use in photographic, medical, structural and fiber applications.

21 Claims, No Drawings

HIGH MOLECULAR WEIGHT COLLAGEN-LIKE PROTEIN POLYMERS

CROSS-REFERENCE TO RELATED APPLICATIONS

This application is a continuation-in-part of application Ser. No. 07/791,960, filed Nov. 12, 1991, now abandoned, which application is a continuation-in-part of application Ser. No. 07/609,716, filed Nov. 6, 1990, which application claims priority to PCT 89/05616, filed Nov. 7, 1989.

TECHNICAL FIELD

The field of this invention is the production of collagen-like polymers using recombinant techniques.

BACKGROUND

Collagen, a naturally occurring protein, finds wide application in industry. Chemically hydrolyzed natural collagen can be denatured and renatured by heating and cooling to produce gelatin, which is used in photographic and medical applications, among other applications. The chain property of collagen responsible for this phenomenon is its ability to spontaneously form interchain aggregates having a conformation designated as a triple helix. The helices are stabilized by weak interactions between chains, arising from the close proximity of the peptide backbone at locations every third residue occupied by glycine and kinks provided by proline and hydroxyproline at the two positions between glycine. The geometry of the three kinked chains allows for hydrogen bonding within the triple helix. The structure is loose and is readily accessible to interaction with water, small organic and inorganic molecules, other proteins, and cells. Although collagen consists of many different amino acid sequences, one of the more structurally stable segments exists at the amino and carboxyl terminal ends of the processed collagen Type I chains. These ends consist to a large degree of the repeating tripeptide sequence GPP (the second P is often hydroxylated).

By contrast with natural forms of collagen, recombinantly-produced collagen-like polymers may consist exclusively of a single repeating tripeptide sequence selected from a wide variety of GXY sequences, where X and Y can be any amino acid, whether derived from known natural sequences or not. Collagen-like polymers can also consist of different tripeptide sequences, which are repeated as blocks in the final polymer. Dissimilar blocks can also be used in a repeating fashion to create block copolymers in order to provide additional chemical or biological functionality.

With the advent of recombinant technology, the opportunity arose to produce collagen-like polymers, where the advantageous properties of collagen could be selectively retained, while new capabilities and characteristics could be introduced. The uniqueness of collagen, the repetitive tripeptide, is a challenge for recombinant technology in light of the high repetitiveness of the sequence and the frequent utility of the amino acids glycine and proline in the composition. Genes encoding proteins with high levels of glycine and proline are by necessity composed of high levels of the nucleotides guanidine and cytidine in self complementary sequences. Thus, as one synthesizes the gene, there is substantial opportunity for strands to loop out, single-stranded DNA to be excised, recombination events to occur which can result in loss of segments of the gene, and inefficient transcription and/or translation. Thus, there is substantial interest in developing techniques and compositions which provide the advantageous properties of collagen, while at the same time allowing for stable expression of high molecular weight collagen-like proteins.

RELEVANT LITERATURE

WO 88/05082 and Goldberg, et al. Gene (Amst.) 80:305–314 (1989) describe the preparation of relatively low molecular weight collagen analog proteins. See also PCT/US87/03360 and PCT/US 89/05016 which describe structural protein polymers.

SUMMARY OF THE INVENTION

High molecular weight collagen-like polymers are provided by synthesizing genes, having glycine at every third position, and not more than about 60% of the amino acids present between the glycines are proline. The genes are prepared by synthesizing sequences having a plurality of tripeptide units, ligating the sequences together to provide multimers, cloning the multimers, and finally joining the multimers to provide for genes expressing high molecular weight collagen-like proteins, for the most part, in unicellular organisms.

DESCRIPTION OF THE SPECIFIC EMBODIMENTS

Methods and compositions are provided for producing high molecular weight collagen-like polymers, where glycine is retained as the first amino acid of a triad repeating unit and the other two amino acids are varied, so as to reduce the proline content of the polymer between the glycines to less than 60%, usually to less than about 40%, more usually less than 30%, based on amino acids in the collagen-like protein. The polymers may be varied in a variety of ways, having a single repeating unit, having alternating repeating units, or having blocks of different repeating units. Usually the polymers will have at their 5' and 3' termini sequences which will contribute fewer than about 20%, more usually fewer then about 10%, of the amino acids of the polymers. Genes are synthesized for encoding the collagen-like polymers, inserted into appropriate expression vectors, which are then introduced into expression hosts. The resulting collagen-like polymers may then be isolated, purified, and used in a variety of ways.

The polymers of this invention will be characterized by having a molecular weight of at least about 30 kD (kiloDaltons), more usually at least about 40 kD and preferably at least about 50 kD, usually not exceeding about 150 kD, more usually not exceeding about 125 kD and frequently not exceeding about 100 kD. The polymers will be further characterized in, being like collagen, providing helices, capable of denaturation and renaturation, forming gels, etc. The polymers will preferably have a major proportion of tripeptide triad sequences found in natural collagens, particularly mammalian collagen. The subject polymers may be modified in a variety of ways, by introducing various functional units, where depending upon the functional units, they may be a part of the design, providing for the uniform alternating glycine at the third position or interrupting the uniformity, or may be present at the end of a block of repetitive units. Any of the 20 amino acids may be present, although charged amino acids would usually be present in fewer than 30%, frequently in fewer than 15%, by number in a repetitive sequence.

The subject collagen-like polymers can be widely varied as to their repeating units, the pattern of repeating units, the insertion of interrupting sequences, and the like. At least 75 weight percent, usually at least 80 weight percent, more usually at least 85 weight percent, will be composed of triads (tripeptides with glycine as the first amino acid). Usually at least 50%, more usually at least 80% of the triads will be found in natural collagen, particularly mammalian collagen. The number of triads will usually be at least about 100, more usually at least about 150, and not more than about 500, usually not more than about 400.

The compositions of this invention will be described by formuli, where each capital letter will indicate an amino acid, where the one letter description for an amino acid will indicate that particular amino acid and where a letter which is not within the one letter description will be used to symbolize any amino acid or a designated group of amino acids. The superscripts will indicate that where there are a plurality of triads, the letter symbolic of amino acids may symbolize the same or different amino acid in each of the triads. Subscripts will always intend the number of repeats of the symbol or formula to which the subscript relates.

For the most part, the polymers will be characterized by having as a motif present at least twice in the collagen-like polymer, either contiguous or non-contiguous, a sequence having the following formula:

$$((glyXO)_n\Omega)_m$$

wherein X and O are any amino acids except that X and O are selected to have a proline content of the repetitive sequences of the polymer, usually the entire polymer, of less than about 45% by number, usually of less than about 40%, and may be less than 30%, and greater than about 10%, usually greater than about 15%;

$\Omega$ has from 0 to 50 amino acids, more usually from 0 to 30 amino acids, frequently from 0 to 15, and will usually be a sequence having functional capability and will be other than repetitive GXO;

n will be at least 4 and not more than about 100, more usually not more than about 75, frequently not more than about 50; and m will be at least 1, may be 2, usually at least about 3 and not more than about 20, usually not more than about 12, particularly m is smaller as n becomes larger.

The repetitive sequence of triads will be at least 60%, usually at least 80% by weight of the polymer.

Usually, the total number of different triads in the motif will be at least 2, more usually at least 3, and not more than about 24, more usually not more than about 16 and frequently not more than about 12. The total number of different amino acids in the motif will usually be not more than about 15, more usually not more than about 10. The number of triads including proline will usually be at least 40 number percent, more usually at least 60 number percent and not more than about 98 number percent. Although all of the triads may include one proline, preferably fewer than 85 number percent, usually fewer than 75 number percent, will include proline.

One type of collagen-like polymer will for the most part have the following motif, as a repetitive motif.

$$(glyX^xO^o)_{n^1}\Omega^\Omega)_{m^1}$$

wherein GXO are as defined previously; x and o are the same number and will be in the range of 2 to 10, usually 3 to 8 and often 4 to 6, particularly 2, 3, 5 or 10, which intends that there will be up to and including that many different triads present in the sequence; $\Omega$ has been defined previously; $\Omega$ is 1 to $m^1$ usually not greater than 3, frequently 1 to 2, preferably 1 where $\Omega$ intends different $\Omega$ groups, similar to the definition of x, and $m^1$ is at least 1, may be 2, usually at least about 3, and not more than about 20, usually not more than about 12, particularly as $n^1$ becomes larger; and $n^1$ is at least about 2 and not more than about 100, usually not more than about 75, more usually not more than about 50, generally not more than about 30.

For example, where x is 3, $\Omega$ is O amino acids, and $m^1$ is 1, one would have the formula:

$$((GX^1O^1)(GX^2O^2)(GX^3O^3))_{n^1}$$

where $X^1$ is a particular amino acid, $X^2$ could be the same or different amino acid, etc., and similarly for O; and $n^1$ will generally be at least about 2, more usually about 4, and not greater than about 33, usually not greater than about 25.

One technique for synthesis of the subject compounds lends itself to a particular motif of the formula:

$$\{(\alpha)_a(\beta)_e(\alpha)_{a^1}\}_g$$

wherein:

$\alpha$ has from 1 to 9 triads, usually 2 to 6 triads, preferably 2 to 4 triads, usually at least 1 triad having a proline, more usually at least 2 triads having a proline;

$\beta$ has from 1 to 24 triads, usually 2 to 18 triads, more usually 3 to 9 triads;

e will be at least 3, usually at least 6, and not more than about 50, usually not more than about 36;

g is at least 1 and not more than about 20, usually not more than about 10, more usually not more than about 8;

a and $a^1$ may be the same or different; a will be at least 1 and not more than about 6, usually not more than about 3, except that a or $a^1$ may be 0.

It will be understood that the greater the number of triads present, the lower the number of repeats required to provide the desired molecular weight.

In a preferred embodiment, these extended motifs will have, for the most part, the following formula:

$$(glyU^u\Omega^\pi)_p(glyX^xO^o)_{n^1}(glyU^u\Omega^\pi)_p\Omega^\Omega)_{m^1}$$

G $X^x$, $O^o$, $Z^z$, $m^1$ and $n^1$ have all been defined previously:

U and $\pi$ are any amino acids, frequently there being a proline present in at least one of the triads (see also the definitions for X and O, which are included herein);

u and $\pi$ have analogous meaning to x and o, indicating the same or different amino acids in the different triad (tripeptide) units; and p and $p^1$ will be 1 to 6, more usually 2 to 4, and the two p's may be the same or different, usually the same except that p may also be 0;

The amino acids of particular interest other than glycine will include alanine (A), isoleucine (I), leucine (L), valine (V), serine (S), threonine (T), asparagine (N), glutamine (Q), lysine (K), arginine (R), aspartic acid (D), glutamic acid (E), histidine (H), and proline (P), preferably there being at least one of a neutral polar amino acid, e.g., S or T, or a neutral aliphatic amino acid, e.g., A, I, L, or V. Usually, the aromatic hydrophobic amino acids will be avoided, e.g., F, Y and W, and the aliphatic hydrophobic amino acids (L, V, I), will usually be used, if at all, when a proline is present. For structural considerations, triad sequences containing proline, alanine, valine, serine, threonine, glutamine, or asparagine in the X or O positions form more stable triple helices. Increased stability is also conferred by triads containing hydroxyproline in the O position. Triads containing tryptophan and tyrosine are usually not utilized. For higher order assembly of triple helices, triads containing glutamic acid or aspartic acid at either the X or O positions, but especially at the X position, and triads containing lysine or arginine, at either the X or O position, but especially at the O position are preferred.

Of particular interest is where at least one triad has proline at a second position, more preferably that two triads have proline at second positions or at least one triad has proline at a third position, sometimes having two triads having proline at a third position, there frequently being at least two triads having a proline at either the first and second position. For the most part, at least 30%, more usually at least 50% of the triads in the motifs will have proline at a second or third position and there may be some triads with proline at both positions, usually not more than 35 number percent.

The choice of triads utilized in a recombinant collagen like polymer are chosen in order to affect properties such as helix stability, hydration, solubility, gel point, biodegradation, and immunogenicity. For example, in order to minimize immunogenicity, triads are utilized consisting of amino acids with simple side chains such as glycine, alanine, serine, valine, and proline. When more complex amino acids are required, they can be incorporated by utilizing hexapeptide, nonapeptide, or longer triad sequences from natural collagen chains that contain these amino acids.

To a great extent, many of the polymers of the subject invention may be depicted by the following formula:

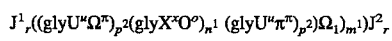

wherein all of the symbols have been described previously, except for:

J$^1$ and J$^2$ which are the same or different and are amino acid sequences of from about 1 to 40 amino acids, more usually from about 1 to 30 amino acids, and may be any sequence of convenience;

the two r's are the same or different and are 0 or 1;

the two p$^2$'s are the same or different, and are 0 or p$^1$.

A variety of repetitive sequences defining the motifs may be illustrated by the following sequences indicated by one letter amino acid designation:
GAPGPAGPK SEQ ID NO:1; GAPGPAGPPGAH SEQ ID NO:2; GSPGAPGPA SEQ ID NO:3; GAPGPAGSRGD-PGPA SEQ ID NO:4; GANGAPGPAGPAGAPGPP SEQ ID NO:5; GAQGPAGPGGAPGPAGPG SEQ ID NO:6; GAPGPAGAS SEQ ID NO:7; GPAGAPGSRGDP-GAPGPP SEQ ID NO:8; GVSGPRGPAGAPGPP SEQ ID NO:9; and GAQGPAGPG SEQ ID NO:10

Triads of particular interest include GAP, GPA, GPP, GAS, GPG, GPS, GAQ, GSP, GSQ, GLQ, GPR, GPK, GAK, GAR, GER, GDR, GEP, GDA, GAH and GEA, where combinations of these triads with other triads are of particular interest, there being at least about 30 number percent, usually at least about 50 number percent of the triads, more usually at least about 60 number percent, frequently at least 80 number percent, coming within the indicated triads. In addition, while the number of triads in any one unit may vary widely, desirably the number will be 3, 5 or a multiple thereof.

Sequences defining the GUB sequences indicated by one letter amino acid designation include:

GAHGPAGPK SEQ ID NO:11; GAHGPAGPR SEQ ID NO:12; GAVGAPGPK SEQ ID NO:13; GPAGAPGEP SEQ ID NO:14; and GVSGPRGAP SEQ ID NO:15

The genes may be synthesized with the method described in PCT/US87/02822. Particularly, the genes are synthesized in accordance with the following protocol. Relatively short oligonucleotide strands are synthesized generally coding for at least 12 amino acids, and usually not more than about 60 amino acids. The complementary strands are annealed, cloned, and sequenced to establish that the correct sequences have been obtained. The ends may be blunt or staggered, usually staggered. The sequences are then multimerized and ligated and inserted into a cloning vector. After transforming into an appropriate host, the clones are analyzed for the oligomerization of the units and appropriate sized units are selected and used for expression. When flanking repetitive units of different sequences are desired, the sequence encoding the motif may be inserted at an appropriate restriction site between the flanking repetitive units, so that subsequently the gene may be excised with the appropriate flanking units. The resulting sequence encoding the motif with the flanking units may then be excised, oligomerized, and, as before, cloned and identified as to having the desired sequence and size.

The subject proteins are produced by transforming an appropriate unicellular host, such as E. coli, B. subtilis, yeast, S. pombe, S. cerevisiae, etc., fungi, Neurospora, Aspergillus, etc. A wide variety of expression vectors have been described in the literature and need not be exemplified here. The expression vector may provide for an inducible or constitutive promoter, whereby the subject proteins may be continuously expressed or expressed only after induction. Numerous expression vectors have appropriate promoters, termination sequences, and polylinkers between the initiation and termination sequences, so that one may conveniently insert the desired gene into the polylinker to be under the transcriptional control of the promoter. In addition, the vectors may have one or more markers, which allow for selection in the transformed host. The vector may also allow for extrachromosomal maintenance or integration into the genome. The markers may provide for resistance to a toxin, e.g. an antibiotic, or complementation of an auxotrophic host to prototrophy. The choice of expression vector will depend upon on a number of factors, such as the host, economy, ease of manipulation, and the like.

Once the expression vector has been cloned, it will normally be analyzed to ensure that the gene is present and has not undergone any modification. The expression host can then be grown up in an expression media and after sufficient time, the cells lysed and the protein isolated. In some cases, the protein will be relatively insoluble and, therefore, may be separated from cellular debris by various convenient means, e.g. centrifugation. Depending on the degree of purity, the protein may be used as is, or may be further purified by extraction using a variety of solvents to extract out the impurities, while leaving the desired product in insoluble form. If desired, dilute acid solution may be used for solubilizing the protein and then precipitating the protein by dialysis. The conditions employed will vary with the particular protein produced, its solubility, the nature of the host, the nature of the contaminants, the ultimate use, and the like.

Small peptides may be prepared which include small segments of the collagen-like polymers, e.g., 15 to 36 amino acids. These segments may be used as haptens, by conjugating the segment to an appropriate immunogen, and the resulting immunogen used for production of antisera or monoclonal antibodies specific for the sequence. Thus, antibodies may be produced which specifically bind to the collagen-like polymers of the subject invention. Depending on the solubility of the subject polymers, the antibodies may be used for affinity purification, identification of the polymers on Western blots, or non-covalently crosslinking of the polymers to produce novel structures and the like.

The subject compositions may find use for a variety of applications, for structural units, in medicine, and the like. The subject collagen-like polymers are useful in the formulation of materials, such as fibers, membranes, films, coatings, hydrogels, colloid suspensions and molded articles, imparting unique characteristics to these materials and to a variety of surfaces from either naturally occurring or synthetic sources, the characteristics usually being associated with water absorption, biocompatibility, or interaction with non-protein compounds of either organic or inorganic nature, e.g. silver halide, dyes, etc. Coatings of 1 to 100 mil may find use, with adherency to a variety of surfaces from naturally occurring and synthetic sources. Distinctive properties of these polymers are their thermal reversible gelation at specific temperatures, their inherent biocompatibility and their bioresorption. Therefore, the subject polymers may find application in photographic films, as wound dressings, allowing for neovascularization, eye applications, bone cements, matrices for artificial organs, membranes, coatings for growing cultures, implantable or injectable drug delivery systems, and the like.

Furthermore, since natural collagen is cross-linked it cannot be redissolved for spinning, shaping, etc. without digestion and molecular weight reduction. Thus, the collagen-like polymers retain the desired collagen characteristics and are capable of being processed.

The following examples are offered by way of illustration and not by way of limitation.

EXPERIMENTAL

Methods for the Production of High Molecular Weight Collagen-Like Protein Polymers

Example 1

DNA Preparation Methods

1. Preparation of plasmid DNA from *E. coli*.

A. Small scale. Plasmid DNA was prepared from 1.5 ml cultures by either the boiling procedure or the alkaline lysis method (Maniatis et al., Molecular Cloning: A Laboratory Manual, Cold Spring Harbor Laboratory, Cold Spring Harbor, (1982).

B. Large scale. A plasmid-carrying strain was grown overnight in 1 liter of Luria broth with the appropriate antibiotic. The cells were collected by centrifugation at 10,000×g for 5 minutes and resuspended in 10 ml of ice cold TE (10 mM Tris-HCl pH 8, 1 mM EDTA). The cells were centrifuged again, resuspended in 4 ml of TES (TE and 25% w/v sucrose) and homogenized by vortexing. The samples were kept on ice for the following steps. Lysozyme (1 ml of 10 mg/ml) was added to the cell suspension and incubated for 5 minutes before the addition of 2 ml of 0.5M EDTA pH 8. After 10 minutes incubation, 50 ml of proteinase K (40 mg/ml) were added followed 10 minutes later with 15 ml of lysing buffer (0.1% Triton X-100, 1 mM EDTA, 50 mM Tris-HCl pH 8). After 15–20 minutes, the cell lysate was centrifuged at 35,000×g for 90–120 minutes. The supernatant (19.8 ml) was transferred to a plastic tube with 20 mg of CsCl and 400 µl of ethidium bromide (10 mg/ml). After dissolution, the mixture was divided into two polyallomer ultracentrifuge tubes, sealed with heat and centrifuged in a Beckman Ti 65 motor at 60,000 rpm for 24 hours. The lower plasmid DNA band was removed from the tube with a hypodermic needle. The ethidium bromide was extracted three times with an equal volume of NaCl-saturated isopropanol. Two volumes of $H_2O$ were added to the DNA solution, and then the DNA was precipitated with ethanol.

2. Deproteinization.

Phenol extraction was performed on a convenient volume of DNA sample, typically between 100 µl to 10 ml. The DNA sample was diluted in 0.01M Tris-HCl pH 7.5, 1 mM EDTA and an equal volume of water-saturated phenol was added. The sample was vortexed briefly and placed on ice for 3 minutes. After centrifugation for 3 minutes in a microfuge, the aqueous layer was removed to a new tube and extracted once with an equal volume of chloroform:isoamylalcohol (24:1).

3. Ethanol precipitation.

DNA in an aqueous buffer was concentrated by ethanol precipitation. To the DNA sample was added 1/10 volume of 3M sodium acetate pH 7.5 and 2–3 volumes of cold ethanol. The DNA was precipitated for 30 minutes at −70° C. or overnight at −20° C. and then pelleted by centrifugation in the microfuge for 15 minutes at 4° C. The pellet was washed once with 200 µl of cold 80% ethanol and precipitated again for 10 minutes at 4° C. After air drying or lyophilization, the pellets were resuspended in the appropriate buffer.

4. Phosphatase treatment of DNA.

A. Phosphatase treatment of DNA was performed by adding 1 µl (25 units) of calf intestinal phosphatase (Boehringer Mannheim) directly to the restriction enzyme digestion reaction and continuing the incubation for 30 minutes at 37° C. The phosphatase was inactivated for 60 minutes at 65° C. prior to deproteinization by phenol extraction.

B. Phosphatase treatment of DNA was also performed by resuspending ethanol precipitated DNA from the restriction enzyme digest in 20 mM Tris-HCl pH 8.0, 10 mM $MgCl_2$ to a final DNA concentration of 20 µg/ml. Shrimp Alkaline Phosphatase was added at 2 U/µg of DNA and the mixture was incubated at 37° C. for one hour, heat inactivated for 20 minutes at 65° C. and then passed through a Probind filter (Millipore) by microfuging for 30 minutes at 12,000 RPM. The DNA was then ethanol precipitated and resuspended in suitable buffer.

5. Phosphorylation of DNA.

Phosphorylation before annealing was performed by using Polynucleotide Kinase 3'-phosphatase-free (Boehringer Mannhaim). The reaction was carried out at 37° C. for 30 minutes in a 50 µl reaction volume containing: 12.5 µg DNA, 5 µl 10× kinase buffer (0.5M Tris pH 7.5, 10 mM Spermidine, 0.1M $MgCl_2$, 150 mM DTT, 1 mM EDTA), and 2 µl Polynucleotide Kinase (10 u/µl). After phosphorylation, salts and glycerol were removed from the DNA strands using a Bio-Spin 6 column (BioRad) equilibrated in TEAB.

6. Fill-in reaction with DNA polymerase 1.

DNA was resuspended in buffer containing 50 mM Tris-HCl pH 7.4, 50 mM KCl, 5 mM $MgCl_2$, and 400 mM each of the four deoxynucleotide triphosphates. Ten units of Klenow DNA polymerase (BRL) were added, and the reaction was allowed to proceed for 15 minutes at room temperature. The DNA was then phenol extracted and ethanol precipitated.

7. Digestion with restriction endonucleases.

DNA was digested with restriction endonucleases (REN) in 1×"AA" buffer [10× AA buffer is 330 mM Tris-acetate, pH 7.9, 660 mM potassium acetate, 100 mM magnesium acetate, 50 mM dithiothreitol (DTT) and 1 mg/ml bovine serum albumin (nuclease free)]. Whenever possible, the concentration of DNA was kept below 1 μg/25 μl. Incubation was at 37° C. for 1–4 hours for most restriction endonucleases except for BalI, BanI and NaeI digestions which were incubated overnight.

8. Analytical agarose gel electrophoresis of DNA.

To DNA samples for gel analysis was added 0.2 volumes of loading buffer (5 × electrophoresis buffer, 0.01% bromphenol blue dye, 50 mM EDTA, and 50% glycerol). Then the samples were loaded into lanes of a horizontal submerged electrophoresis unit containing a 1.0% (w/v) agarose gel. The electrophoresis buffer was either 1×TAC or ½×TBE. The 1×TAC is 40 mM Tris-base, 10 mM EDTA, adjusted to pH 7.8 with acetic acid. The ½×TBE is 0.045M Tris-base, 0.045M boric acid, 1 mM EDTA, pH 8. The gel was run at 40–50 V for 18 hours, then removed and stained with 0.5 g/ml ethidium bromide for 30 minutes. The DNA bands were visualized on a long wavelength UV transilluminator.

9. Preparative agarose gel electrophoresis.

The procedures and materials are the same as for the analytical agarose gel electrophoresis. The only difference is the use of low melting point (LMP) agarose, ranging in concentration from 0.5 to 2.5% (w/v) depending on the size of the DNA fragment to be purified. DNA restriction fragments were excised from the LMP agarose gels after visualization with ethidium bromide. For agarose ligation the buffer used was 1×TAE (50 mM Tris Acetate).

10. NACS purification.

Gel fragments containing DNA were melted at 70° C. for 5 minutes and diluted approximately 5 fold with TE1 (10 mM Tris-HCl pH 7.5, 0.2M NaCl). The gel solution was applied to a NACS column (BRL). The column was washed with 5 ml of the same buffer. The bound DNA was eluted with 300 μl of either TE2 (10 mM Tris-HCl pH 7.5, 1.0M NaCl) for DNA fragments smaller than 1000 bp or TE3 (10 mM Tris-HCl pH 7.5, 2M NaCl) for larger fragments. The eluted DNA was concentrated by ethanol precipitation.

11. DNA ligation.

Reactions for ligating cohesive ends contained: 1 μg DNA, 1×AA buffer (see step 6, above) 1 mM ATP and 20 units of T4 DNA ligase (BRL) in a 20 μl final reaction volume. The ligation was allowed to proceed for 16–18 hours at 15° C. or 1–2 hours at room temperature. For blunt-ended ligations the reactions contained 1 μg DNA, 25 mM Tris-HCl pH 7.5, 5 mM $MgCl_2$, 5 mM DTT, 0.25 mM spermidine, 200 ng BSA, 1 mM hexamine cobalt chloride (HCC), 0.5M ATP and 400 units T4 DNA ligase (NEB) in a 20 μl reaction volume. The ligation was allowed to proceed for 30 minutes to 1 hour at room temperature.

12. Agarose DNA ligation.

The agarose was melted at 65° C., the temperature was then lowered to 37° C. and ligation buffer (5X= 100 mM Tris-HCl, pH 7.5, 50 mM $MgCl_2$, 50 mM DTT, 1 mM ATP) was added; the tube was then placed at room temperature and ligase was added (1000 units T4 DNA ligase (NEB), the reaction volume was usually 50 μl. The reaction was incubated at 15° C. for 16–18 hours.

mRNA Methods

1. Preparation of mRNA.

mRNA was prepared using a modified procedure described by Summers, W. C. (*Anal. Biochem.* 33:459–463 (1970). Cells were grown at 30° C. or 42° C. in LB medium supplemented with kanamycin (50 μg/ml). 10 ml of cells at $OD_{600}$ 1.0 were spun and the cell pellet was resuspended in 10 ml of protoplasting buffer (15 mM Tris-HCl pH 8.0, 0.45M sucrose, 8 mM EDTA); 80 μl of lysozyme at 50 mg/ml were added and the mixture was then incubated on ice for 15 minutes. The cell suspension was spun for 5 minutes at 7,000 RPM in an SS-34 rotor using an RC-5B centrifuge. The pellet was resuspended in 0.5 ml of lysing buffer (10 mM Tris-HCl pH 8.0, 10 mM NaCl, 1 mM Na-Citrate, 1.5% w/v SDS) and 15 μl of DEPC. The suspension was mixed gently and then transferred to a 1.5 ml Eppendorf tube, incubated at 37° C. for 5 minutes and then chilled on ice. 250 μl of saturated NaCl (40% w/v) were added, mixed gently, and the incubation, on ice, was prolonged for an additional 10 minutes. The slurry was spun at 4° C. for 15 minutes. The supernatant was placed in two 1.5 ml tubes and 1 ml of 100% ethanol was added to each. The RNA was precipitated in the cold and then spun at 4° C. for 20 minutes. The pellets were rinsed in 70% ethanol and dried. The RNA was then resuspended in 0.1 ml $H_2O$ and $OD_{260}$ and $OD_{280}$ were taken to measure the recovery and purity of the RNA. The average recovery of total RNA (5% mRNA, 95% tRNA+ rRNA), from 10 ml of growing cells, was between 0.5 and 1.0 mg.

2. Northern blot analysis.

The RNA, purified as described above, was run on agarose gel and transferred to nitrocellulose following the procedure described in Maniatis et al., Molecular Cloning: A Laboratory Manual, Cold Spring Harbor Laboratory, Cold Spring Harbor (1982), pp 202–203, using 10X SSC as transfer buffer. The ECL gene detection system kit (Amersham) was used for labelling of the probe, hybridization conditions and detection. The procedures were executed as described in: ECL gene detection system RPN2101, version 2, Amersham International plc.

Bacterial Transformation Methods

1. Preparation of transformation-competent *E. coli* cells.

A culture of 200 ml of sterile L broth was inoculated with a small loopful of *E. coli* cells. This was incubated with shaking at 37° C. until the $OD_{600}$ was approximately 0.5. The culture was placed on ice for 10 minutes and centrifuged at 6,000×g for 10 minutes. The cell pellet was resuspended in 100 ml of ice-cold 0.1M $MgCl_2$, kept on ice for 30–40 minutes and centrifuged again. The pellet was resuspended in 2 ml of ice-cold 100 mM $CaCl_2$, transferred to a sterile test tube and incubated on ice for 24 hours. The competent cells were then aliquoted and stored at −70° C.

2. Transformation of *E. coli*.

An aliquot of frozen competent cells was thawed on ice. To 50 μl of cells, 0.1 to 1 μg of DNA was added and the mixture was incubated on ice for 30 minutes. The tube was removed from ice and placed in a 42° C. bath for 2 minutes. L broth (1 ml) was added and the transformation mix incubated with shaking at the desired temperature (usually 30° C. or 37° C.) for 2 hours. Then one-tenth of the transformation was plated on L broth plates containing the appropriate antibiotic and, when necessary, XGAL and IPTG were added.

Antibody Production, Protein Chemistry and Electrophoresis of Proteins

1. Preparation of antibody to artificially synthesized Peptides.

A synthetic peptide of sequence GAHGPAGPKGAHG-PAGPKGAPGPAGPPGAPGPAGPP SEQ ID NO:16 (SequenceD-$C_2A_2$) where $C_2A_2$ defines an amino acid sequence motif indicated by one letter amino acid designation was coupled to keyhole limpet hemocyanin for use as an immunogen. The material was sent to Antibodies, Inc. for preparation of antibodies in rabbits. Peptide conjugates at a concentration of 1 mg/ml in complete Freund's adjuvant were used to immunize rabbits at day 0. Animals were re-injected with antigen in Freund's incomplete adjuvant at day 30 and titered at day 60. Positive sera was detected using a microtiter RIA using the synthetic peptide as antigen. Kagen and Glick (1979), in Methods of Radioimmunoassay, Jaffe and Berman (eds.), Academic Press, p 328. Antisera was obtained that reacted with synthetic peptides of the SequenceD1 and SequenceD2 sequences.

Following the procedure described above an additional peptide was synthesized having the sequence (GAPGPAG-PPGSRGDPGPP)$_2$ SEQ ID NO:17 (SequenceD-(AB)$_2$), which was also coupled to keyhole limpet hemocyanin for use as an immunogen. Polyclonal antisera were then prepared as described above, which bound to the synthetic peptide of the SequenceD3 sequence.

Following the procedure described above an additional peptide was synthesized having the sequence (GAPGAPG-SQGAPGLQ)$_2$ YMK SEQ ID NO:18 which was also coupled to keyhole limpet hemocyanin for use as an immunogen. Polyclonal antisera were then prepared as described above, which bound to the synthetic peptide of the CLP 3.1 sequence.

2. Polyacrylamide gel electrophoresis of proteins.

Approximately $10^9$ E. coli cells from growing cultures were pelleted by centrifugation at 10,000×g for 5 minutes. The cell pellets were resuspended in 100 to 500 μl of 2X sample buffer (100 mM Tris-HCl pH 6.8, 4% SDS, 10% β-mercaptoethanol, 60% glycerol or sucrose) and sonicated for 30 seconds using a Tekmar sonic disrupter. Samples were boiled for approximately 5 minutes and 20 to 100 μl of the cell lysates were loaded on an SDS-polyacrylamide gel (7.5 to 16% w/v). The gels were prepared following the procedure of Laemmli (*Nature*, 27:80–685 (1970)). The proteins in the gels were stained with 2% Coomassie brilliant blue in 10% methanol, 7.5% acetic acid for 1 hour and destained in 10% methanol, 7.5% acetic acid overnight.

3. Protein expression analysis.

An overnight culture which had been grown at 30° C. was used to inoculate 50 ml of LB media contained in a 250 ml flask. Kanamycin was added at a final concentration of 50 μg per ml and the culture was incubated with agitation (200 rpm) at 30° C. When the culture reached an OD$_{600}$ of 0.8, 40 ml were transferred to a new flask prewarmed at 42° C. and incubated at the same temperature for approximately 2 hours. The cultures (30° C. and 42° C.) were chilled on ice and OD$_{600}$ was taken. Cells were collected by centrifugation and then divided in 1.0 OD$_{600}$ aliquots and used to perform western analysis using the appropriate antibodies.

4. Immunoblotting of proteins in gels.

After protein electrophoresis, one of the flanking glass plates was removed from the polyacrylamide gel. The gel surface was wetted with transfer buffer (25 mM Tris-HCl, 192 mM glycine, 20% methanol). A piece of nitrocellulose paper (Sartorius, SM11307) was saturated with transfer buffer and laid on the gel. Air bubbles between the filter and the gel were removed. The gel and nitrocellulose filter were placed in the transfer unit as specified by the manufacturer (Bio-Rad). Transfer was allowed to proceed at 200 mA for 3–4 hours. Then the nitrocellulose filter was removed and stained with Amido-Schwartz for 3 minutes (0.05% Amido black, 45% deionized H$_2$O, 45% methanol, 10% acetic acid) and destained in H$_2$O. The filter was incubated for at least 10 minutes at room temperature in "BLOTTO" (5% w/v nonfat dry milk, 50 mM Tris-HCl pH 7.4, 0.9% w/v NaCl, 0.2% w/v sodium azide). The filter was placed in serum appropriately diluted (1:50 to 1:500) in 0.5X Blotto (2.5% nonfat dry milk, 50 mM Tris-HCl pH 7.4, 0.9% NaCl, 0.2% sodium azide) and was gently agitated for approximately 16 hours at room temperature. The filter was washed for 1 hour with 5 changes of TSA (50 mM Tris-HCl pH 7.4, 0.9% NaCl, 0.2% sodium azide). The blot was placed in 15 ml of 0.5X BLOTTO solution containing 1×10$^7$ cpm of $^{125}$I-protein A and gently agitated for 2 hours at room temperature. The filter was washed for 2 hours with a minimum of 7 changes of TSA, rinsed once with deionized H$_2$O and air dried. The blot was covered with Saran wrap and autoradiographed.

5. Amino Acid Analysis.

Amino acid compositions were determined by the PTC derivatization procedure of Henrickson and Meredith (1984). Protein samples were hydrolysed with 5.7N constant boiling HCl at 108° C. for 24 hours in vacuo. After reaction with PITC, amino acid derivatives were detected at 254 nm by HPLC reverse phase chromatography using a Waters 100E system and a Supelco C18 column (4.6 mm×25 cm) with a linear gradient of 0–50% acetonitrile in 0.1M NH$_4$OAc pH 6.78 as a mobile base. Henrickson, R. L. and Meredith, S. C. (1984) Amino Analysis by Reverse Phase High Performance Liquid Chromatography., *Anal. Biochem.* 137:65–74.

6. Peptide Synthesis.

Synthetic peptides were prepared by solid phase synthesis on an Applied Biosystems Model 430A Peptide Synthesizer using the standard symmetric anhydride chemistry as provided by the manufacturer. The coupling yield at each step was determined by the quantitative ninhydrin procedure of Sarin et al., (1981). The synthetic peptide was cleaved from the solid support and amino acid blocking groups were removed using anhydrous HF (Stewart and Young, (1984)). Crude peptides were desalted by chromatography over Sephadex G-50. Sarin, V. K., Kent, S. B. H., Tam, J. P. and Merrifield, R. B. (1981) *Anal. Biochem.* 237:927–936. Stewart, J. M. and Young, J. D. (1984) Solid Phase Peptide Synthesis, Pierce Chemical Company, Rockford, Ill. pp 85–89.

Synthetic DNA Methods

1. In vitro DNA synthesis.

The N,N-diisopropyl phosphoramidites, controlled-pore glass columns and all synthesis reagents were obtained from Applied Biosystems, Foster City, Calif. Synthetic oligonucleotides were prepared by the phosphite triester method with an Applied Biosystems Model 381A DNA synthesizer using a 10-fold excess of protected phosphoramidites and 1 μmole of nucleotide bound to the synthesis support column. The chemistries used for synthesis are the standard protocols recommended for use with the synthesizer and have been described (Matteucci et al., *J. Amer. Chem. Soc.*, 103:3185–3319 (1981)). Deprotection and cleavage of the oligomers from the solid support were performed according to standard procedures as described by McBride et al., *Tetrahedron Letters*, 24:245–248 (1983). The repetitive yield of the synthesis as measured by the optical density of the removed protecting group as recommended by Applied Biosystems (1984) was greater than 97.5%. The crude oligonucleotide mixture was purified by preparative gel electrophoresis as described by the Applied Biosystems protocols of Nov. 9, 1984 (User Bulletin No. 13). The acrylamide gel concentration varied from 10 to 20% depending upon the length of the oligomer. The purified oligomer was identified by UV shadowing, excised from the gel and extracted by the crush and soak procedure (Smith, *Methods in Enzymology* 65:371–379 (1980)).

2. Sequencing of DNA.

DNA sequences were determined by the methods described in the following references: Maniatis et al., *Molecular Cloning: A Laboratory Manual.* Cold Spring Harbor Laboratory, Cold Spring Harbor, N.Y.; Norrander et al., *Gene* (1983) 26:101–106; Sanger et al., *Proc. natl. Acad. Sci. USA* (1977) 74:5463–5467; Biggin et al., *Proc. Natl. Acad. Sci. USA* (1983) 80:3963–3965; and Sanger et al., *FEBS Letters* (1978) 87:107–110.

Fragments containing the region of interest were cloned into the multiple cloning site of M13mp18 or M13mp19 (Maniatis et al., (1982), and Norrander et al., (1983)).

tains two recognition sites for FokI REN in its MCS (multiple cloning site).

Two oligonucleotide strands containing these sites were synthesized and purified as described in Example 1.

```
              FokI                              FokI     ScaI
5'-GTGCTGCGGATGCTCGAGATGGTGCATGCATGTACATCCGAGTACTTCGAT           0.A)
                                       SEQ ID NO:22

3'-      ACGCCTACGAGCTCTACCACGTACGTACATGTAGGCTCATGAAGCTA      0.B)
                                       SEQ ID NO:23
```

Single-stranded DNA was prepared and sequenced by the primer extension method (Sanger et al., (1977) and Biggin et al., (1983)) using $^{35}$S-deoxyadenosine 5'-(alpha-thio)-triphosphate (New England Nuclear) as label. In some cases, reverse transcriptase (Molecular Genetics) was used to extend the primer, using the dideoxy:deoxynucleoside triphosphate ratios utilized by Zagursky et al. (*Gene Anal. Tech.* (1985) 2:89–94). Deoxyadenosine triphosphate labeled with either $^{32}$P or $^{35}$S was used in these reactions. Compression artifacts which appeared in some G-C rich sequences were overcome by eliminating deoxyguanosine triphosphate from the G reaction, and using deoxyinosine triphosphate (P-L Biochemicals) at a final concentration of 37.5 μM instead. In the other mixes, the concentration of dideoxyGTP in the G reaction was 0.5 mM. All sequences were run on 6 or 8% polyacrylamide gels containing 8M urea (Sanger et al., (1978)). Primers used for sequencing were purchased from P-L Biochemicals.

3. Dideoxy DNA sequencing of double stranded plasmid DNA.

Plasmid DNA was prepared as described previously (Preparation of plasmid DNA from *E. coli*, Small scale, Maniatis et al.). Primers were synthesized using a DNA synthesizer as described previously, and were annealed to the plasmid DNA following the procedure described above for M13 sequencing. The sequencing reactions were done using Sequenase (United States Biochemicals) and the conditions were as recommended by the supplier. All sequences were run on polyacrylamide gels as described above.

Example 2

TABLE 1

STRUCTURE OF SEQUENCE D 1, 2 & 3

| SEQUENCE D1 | $(C_2A_{24}C_2)_4$ |
| SEQUENCE D2 | $(C_2A_{12}C_2)_8$ |
| SEQUENCE D3 | $(C_2(AB)_{12}C_2)_4$ | where:
A = GAPGPAGPP SEQ ID NO:19
B = GSRGDPGPP SEQ ID NO:20
C = GAHGPAGPK SEQ ID NO:21

DNA Design

Due to the complexity of the SequenceD polymer structures the design of the gene monomers was as follows:
1. design and synthesis of $C_2$ units (5' and 3')
2. design and synthesis of A units
3. design and synthesis of AB units Plasmid pPT 0134 Construction The acceptor vector PPT 0134 was designed and constructed specifically to accommodate the construction requirements of the DCP polymer genes. This vector con- After annealing, the two oligonucleotide strands were ligated with pSY 937 (see patent application number PCT/US87/02822) which had been digested with BanI and EcoRV RENs. The product of the ligation mixture was transformed into *E. coli* and selected on bacterial plates containing the antibiotic chloramphenicol. Plasmid DNA from individual colonies was analyzed on agarose gel electrophoresis after digestion with ScaI and StuI RENs. One plasmid pPT 0124 contained the expected DNA fragment.

The new MCS was then moved to plasmid pSY 1367. This plasmid is a derivative of pSY 1299 (see patent application number PCT/US87/02822). Plasmid pSY 1299 was digested with NciI REN and the large DNA fragment was purified by agarose gel electrophoresis and NACS purification. The purified DNA fragment was treated with DNA Polymerase (see Example 1), ligated, then digested with FokI prior to transformation in *E. coli* strain HB 101. Plasmid DNA from single colonies was purified and analyzed by restriction digests. One plasmid, pSY 1366, was found to be correct and lacking the only FokI site present in pSY 1299.

Two oligonucleotide strands were synthesized and purified as described in Example 1:

```
    (BanII)              FokI
5'-       CTACATGTGTTACACATCCCGTGC              1.A)
                    SEQ ID NO:24

3'-CCGAGATGTACACAATGTGTAGGGCACG             1.B)
                    SEQ ID NO:26
```

Oligonucleotide strands 1.A and 1.B were annealed and ligated with the DNA of plasmid pSY 1366 which had been digested with BanII and FspI RENs. The products of this ligation reaction were transformed into *E. coli* strain HB101. Plasmid DNA from transformed colonies was purified and digested with FokI. Clones which linearized with FokI were sequenced. Plasmid pSY 1367 contained the desired MCS sequence and was chosen for subsequent constructions.

Plasmids pPT 0124 and pSY 1367 were digested with NruI and NcoI and the DNA fragments were purified by agarose gel electrophoresis and NACS purification. The small fragment (approximately 500 bp) from pPT 0124 was ligated with the large fragment from pSY 1367. The product of the ligation mixture was transformed into *E. coli*. Plasmid DNA from single colonies was purified and analyzed by restriction digests and DNA sequencing. One plasmid, pPT 0134, contained the desired sequence and was used as the acceptor vector for the SequenceD constructions.

Synthesis and Assembly of the C Units

Four oligonucleotide strands were synthesized and purified as described in Example 1. Each pair of oligonucleotide strands encodes a $C_2$ unit, either the 5' or 3' $C_2$ unit.

5'-GTGCTCACGGCCCAGCAGGTCCGAAGGGCGCGCATGGCCCAGCAGGCCCGAAAGGTGCC        2.A)
                                SEQ ID NO:26

3'-       AGTGCCGGGTCGTCCAGGCTTCCCGCGCGTACCGGGTCGTCCGGGCTTTCCACGGCACG   2.B)
                                SEQ ID NO:27

5'-GTGCCCATGGCCCAGCAGGACCGAAAGGAGCTCACGGTCCGGCAGGTCCGAAAG              2.C)
                              SEQ ID NO:28

3'-       GTACCGGGTCGTCCTGGCTTTCCTCGAGTGCCAGGCCGTCCAGGCTTTCCACG         2.D)
                                SEQ ID NO:29

Oligonucleotide strands 2.A and 2.B were annealed and ligated with the DNA of plasmid pPT 0134 which had been digested with FokI REN. The products of this ligation reaction were transformed into *E. coli* strain HB101. Plasmid DNA from transformed colonies was purified and digested with SfiI. Clones which linearized with SfiI were sequenced. Plasmid pPT 0135 contained the desired $C_2$ sequence and was chosen for subsequent constructions.

Strands 2.C and 2.D were annealed, ligated, and transformed as were strands 2.A and 2.B. Plasmid DNA from transformed colonies was purified and digested with BanII REN. Clones which linearized with BanII were sequenced. Plasmids pPT 0137 and pPT 0138 contained the correct $C_2$ DNA sequence.

Plasmid pPT 0135 and pPT 0137 were digested with BanI and StuI RENs. The large fragment from pPT 0135, containing the $C_2$ (strands A+B), was ligated with the small fragment of pPT 0137 containing the $C_2$ fragment (strands C+D). The ligation products were transformed into *E. coli* strain HB101. Plasmid DNA from transformants was purified and two digestions were performed, SfiI-StuI and BanII-StuI RENs, respectively. Clones that released a DNA fragment of approximately 800 bp in both digestions were sequenced. Plasmid pPT 0140 contained the correct $C_2C_2$ sequence, as shown in Table 2, and was used for SequenceD gene monomer constructions.

agarose gel electrophoresis and purified using a NACS column (see Example 1). The DNA fragment was self-ligated and the products of the ligation were ligated with pPT 0134 previously digested with FokI REN. The products of the ligation mixture were transformed into *E. coli* strain HB101. Plasmid DNA from transformants was purified and digested with FokI REN. Clones containing DNA inserts of 162 bp corresponding to $A_6$ were selected for sequence analysis. Plasmid pPT 0144 had the expected DNA sequence and was selected for subsequent constructions. Plasmid DNA from pPT 0144 was digested with FokI REN and the two DNA fragments generated by the digestion were separated using agarose gel electrophoresis. The smaller DNA fragment was purified using a NACS column (see Example 1). The DNA fragment carrying the $A_6$ coding sequence was ligated with plasmid DNA pPT 0140 previously digested with FokI. The products of the ligation were transformed into *E. coli* strain HB101. Plasmid DNA from individual colonies was analyzed for inserts containing multiple $A_6$ DNA fragments by digestion with FokI. Several size inserts were found ranging from $A_6$ to $A_{24}$. One clone, pPT 0147 (shown in Table 3) was identified to contain the desired SequenceD 2 gene monomer sequence $C_2A_{12}C_2$ and was used for further constructions.

The clone containing the SequenceD1 gene monomer sequence $C_2A_{24}C_2$ (shown in Table 4), necessary to con-

```
GGTGCTCACGGCCCAGCAGGTCCGAAGGGCGCGCATGGCCCAGCAGGCCCGAAA
CCAGCAGTGCCGGGTCGTCCAGGCTTCCCGCGCGTACCGGGTCGTCCGGGCTTT
 G   A   H   G   P   A   G   P   K   G   A   H   G   P   A   G   P   K

Ban 1
GGTGCCCATGGCCCAGCAGGACCGAAAGGAGCTCACGGTCCGGCAGGTCCGAAA
                                                    SEQ ID NO:30

CCACGGGTACCGGGTCGTCCTGGCTTTCCTCGAGTGCCAGGCCGTCCAGGCTTT
                                        SEQ ID NO:31
 G   A   H   G   P   A   G   P   K   G   A   H   G   P   A   G   P   K
```

SequenceD 1 and 2 Gene Monomer Constructions

Two oligonucleotide strands were synthesized and purified as described in Example 1.

3.A)   5'-GTGCGCCTGGACCGGCTGGTCCAC-CGGGTGCTCCGGGACCTGCAGGCCCGCCAG SEQ ID NO:32

3.B)   3'-CGGACCTGGCCGACCAGGTGGCCCAC-GAGGCCCTGGACGTCCGGGCGGTCCACG SEQ ID NO:33

The two oligonucleotide strands encoding $A_2$(3A & 3B) were annealed and ligated with plasmid DNA pPT 0134 previously digested with FokI REN. The products of the ligation mixture were transformed into *E. coli* strain HB101. Plasmid DNA from transformants was digested with PstI REN and clones that were linearized were sequenced. Plasmid pPT 0142 was found to be correct and used for the multimerization of $A_2$ units.

Plasmid DNA from pPT 0142 was digested with FokI REN and the fragment containing the $A_2$ unit was isolated by struct the SequenceD1 polymer gene, was found to be highly unstable during subsequent passages. This instability was attributed to the high copy number of the acceptor plasmid. For this reason, the gene monomer from this plasmid was recloned into pBR 322 (F. Bolivar, et al. (1977) *Gene* 2:95–113). The plasmid DNA containing the $C_2A_{24}C_2$ gene fragment was isolated from the plasmid by digestion with NruI and EcoRV RENs, agarose gel electrophoresis, and purified on a NACS column. This DNA fragment was ligated with plasmid pBR322 DNA digested with EcoRV and NruI RENs (see agarose ligation in Example 1). The products of this ligation were transformed into *E. coli* strain HB101 and selected on bacterial plates containing the antibiotic ampicillin at 100 μg/ml. Plasmid DNA from individual colonies was analyzed by agarose gel electrophoresis. Clones containing the insert were further analyzed by digestion with several RENs and one, pPT 0153, was chosen for the construction of the SequenceD 1 polymer gene. This plasmid was stable.

```
GGTGCTCACGGCCCAGCAGGTCCGAAGGGCGCGCATGGCCCAGCAGGCCCGAAA
CCACGAGTGCCGGGTCGTCCAGGCTTCCCGCGCGTACCGGGTCGTCCGGGCTTT
GAHGPAGPKGAHGPAGPK
```

$$\begin{bmatrix} \text{GGTGCGCCTGGACCGGCTGGTCCACCGGGTGCTCCGGGACCTGCAGGCCCGCCA} \\ \text{CCACGCGGACCTGGCCGACCAGGTGGCCCACGAGGCCCTGGACGTCCGGGCGGT} \\ \text{G A P G P A G P P G A P G P A G P P} \end{bmatrix}_6$$

Ban
I
```
GGTGCCCATGGCCCAGCAGGACCGAAAGGAGCTCACGGTCCGGCAGGTCCGAAA
                                              SEQ ID NO:34

CCACGGGTACCGGGTCGTCCTGGCTTTCCTCGAGTGCCAGGCCGTCCAGGCTTT
                           SEQ ID NO:35
GAHGPAGPKGAHGPAGPK
```

15

```
GGTGCTCACGGCCCAGCAGGTCCGAAGGGCGCGCATGGCCCAGCAGGCCCGAAA
CCACGAGTGCCGGGTCGTCCAGGCTTCCCGCGCGTACCGGGTCGTCCGGGCTTT
GAHGPAGPKGAHGPAGPK
```

$$\begin{bmatrix} \text{GGTGCGCCTGGACCGGCTGGTCCACCGGGTGCTCCGGGACCTGCAGGCCCGCCA} \\ \text{CCACGCGGACCTGGCCGACCAGGTGGCCCACGAGGCCCTGGACGTCCGGGCGGT} \\ \text{G A P G P A G P P G A P G P A G P P} \end{bmatrix}_{12}$$

Ban
I
```
GGTGCCCATGGCCCAGCAGGACCGAAAGGAGCTCACGGTCCGGCAGGTCCGAAA
                                              SEQ ID NO:36

CCACGGGTACCGGGTCGTCCTGGCTTTCCTCGAGTGCCAGGCCGTCCAGGCTTT
                           SEQ ID NO:37
GAHGPAGPKGAHGPAGPK
```

SequenceD 1 Polymer Gene Construction.

Plasmid from DNA pPT 0153 was digested with AcyI REN and subsequently with FokI REN. The DNA fragment containing the SequenceD 1 gene monomer, 783 bp, was isolated by agarose gel electrophoresis and purified using a NACS column (see Example 1). The monomer gene fragment was ligated with pSY 1262 (see patent application number PCT/US87/02822) which had been digested with BanI REN. The ligation product was transformed into E. coli strain HB101 and selected for growth on bacterial plates containing the antibiotic kanamycin. Plasmid DNA from individual colonies was analyzed for inserts containing multiple SequenceD 1 monomer fragments by digestion with BamHI and PvuII RENs and electrophoresis on agarose gel. One clone, pPT 0164, contained the gene monomer (783 bp); another, pPT 0165, a slightly larger fragment (approximately 1200 bp); and a third, pPT 0166, a gene dimer (1566 bp).

SequenceD 1 Protein Expression Analysis.

E. coli strain HB101 containing plasmid pPT 0164, pPT 0165 or pPT 0166 was grown at 30° C. to an $OD_{600}$ of 0.7 and then shifted to 42° C. for 2.0 hours. The proteins produced by these cells were analyzed by western blot analysis for novel protein bands which reacted with SequenceD-$C_2A_2$ peptide antisera. A band with an apparent molecular weight of approximately 45 kD was observed in the culture containing the plasmid pPT 0164. A band of 68 kD was observed with pPT 0165 and a light smear of bands with pPT 0166.

Because of the low level of detectable expression in the strain containing pPT 0166, the mRNA produced by the SequenceD 1 clones was analyzed. mRNA was prepared as described in Example 1. By northern blot analysis (see Example 1), the SequenceD specific mRNA from all clones, using as a probe the SequenceD2 monomer sequence, was shown to be full length and synthesized at approximately the same level regardless of the SequenceD gene size.

Sequence D1 pPT 0166 561 Amino Acids MW: 46,409 Dalton
MDPVVLQRRDWENPGVTQLNRLAAHPPFASDPM
[(GAHGPAGPK)$_2$ (GAPGPAGPP)$_{24}$ (GAHGPAGPK)$_2$]$_2$
GAMDPGRYQLSAGRYHYQLVWCQK
SEQ ID NO:38

SequenceD 2 Polymer Gene Construction.

Plasmid DNA from pPT 0147 was digested with FokI REN and the digestion fragments were separated by agarose gel electrophoresis. The SequenceD 2 gene fragment of 483 bp was excised and purified by NACS column (see Example 1). The purified fragment was ligated with pSY 1262 which had been digested with BanI REN. The products of this ligation were transformed into E. coli strain HB101 and the transformants were selected for growth on bacterial plates containing the antibiotic kanamycin. Plasmid DNA from individual colonies was purified and analyzed for multiple insertions of the SequenceD 2 gene monomer fragment. Several clones were obtained ranging in size from 500 to 3,000 bp. See Table 5 for the results.

SequenceD 2 Protein Expression Analysis

E. coli strain HB101 containing plasmids pPT 0155 to 0163 were grown at 30° C. to an $OD_{600}$ of 0.7 and then shifted to 42° C. for 2.0 hours. The proteins produced by these cells were analyzed by western blot analysis for a protein band reactive with SequenceD-$C_2A_2$peptide specific antisera. See Table 5 for the results.

TABLE 5

| Sequence D 2 Expression clones | # of repeats | Gene size (in bp) | # of amino acids | Protein band observed (in kD) |
|---|---|---|---|---|
| pPT 155 | 1 | 603 | 201 | no detection |
| pPT 156 | 2 | 1035 | 345 | 40 |
| pPT 157 | 3 | 1467 | 489 | 60 |
| pPT 158 | 4 | 1899 | 633 | 80 |
| pPT 159 | 5 | 2331 | 777 | 100 |
| pPT 160 | 6 | 2763 | 921 | smear |
| pPT 161 | 7 | 3195 | 1065 | no detection |
| pPT 162 | 7+ | 3240 | 1080 | no detection |
| pPT 163 | 7+ | 3420 | 1140 | no detection |

Sequence D 2 pPT 0159 777 Amino Acids MW: 64,094 Dalton
MDPVVLQRRDWENPGVTQLNRLAAHPPFASDPM
[(GAHGPAGPK)$_2$ (GAPGPAGPP)$_{12}$ (GAHGPAGPK)$_2$]$_5$
GAMDPGRYQLSAGRYHYQLVWCQK SEQ ID No: 39

SequenceD 3 Monomer Construction

Four oligonucleotide strands encoding (AB)$_2$ were synthesized and purified as described (see Example 1).

5'-GTGCTCCGGGACCTGCAGAATATTATTCTAGAGGTGACCCAGGACCGCCTG-3'  (4.A)
SEQ ID NO:40

AGGCCCTGGACGTCTTATAATAAGATCTCCACTGGGTCCTGGCGCACCAC 5'  (4.B)
SEQ ID NO:41

5'- GGCCCACCGGGTAGCCGTGGCGATCCGGGACCACCGGGTGCACCTGGCCCAGCGGGTCCGCCTGGAT-3'  (4.C)
SEQ ID NO:42

3'- ACGTCCGGGTGGCCCATCGGCACCGCTAGGCCCTGGTGGCCCACGTGGACCGGGTCGCCCAGGCGGACCTAGATC-5'  (4.D)
SEQ ID NO:43

Oligonucleotide strands 4.A and 4.B were annealed and ligated with the DNA plasmid pPT 0134 (see Example 1) which had been digested with FokI REN. The products of this ligation were transformed into *E. coli* strain HB101. Plasmid DNA from transformed colonies was purified and digested with PstI and StuI. Clones containing a fragment of approximately 800 bp were sequenced. Plasmid pPT 0139, containing the desired sequence of strands 4.A and 4.B, was chosen for subsequent constructions.

Strands 4.C and 4.D were annealed and ligated with the DNA plasmid pPT 0139 which had been previously digested with XbaI and PstI RENs. The products of this ligation were transformed into *E. coli* strain HB101. Plasmid DNA from transformed colonies was purified and digested with NcoI and DraIII RENs. Clones containing a DNA fragment corresponding to the combined insertion of strands 4.A and B and 4.C and D were sequenced. Plasmid pPT 0143, containing the correct (AB)$_2$ DNA sequence, as shown in Table 6, was chosen for further constructions.

GGTGCTCCGGGACCTGCAGGCCCACCGGGTAGCCGTGGCGATCCGGGACCACCG
CCACGAGGCCCTGGACGTCCGGGTGGCCCATCGGCACCGCTAGGCCCTGGTGGC
GAPGPAGPPGSRGDPGPP

XbaI
GGTGCACCTGGCCCAGCGGGTCCGCCTGGATCTAGAGGTGACCCAGGACCGCCT
SEQ ID NO:44

CCACGTGGACCGGGTCGCCCAGGCGGACCTAGATCTCCACTGGGTCCTGGCGGA
SEQ ID NO:45

GAPGPAGPPGSRGDPGPP

Plasmid DNA from pPT 0143 was digested with FokI REN and the fragment containing the (AB)$_2$ gene fragment was isolated by agarose gel electrophoresis and purified on a NACS column. The DNA fragment was then ligated with pPT 0134 that had been digested with FokI REN. The products of the ligation were transformed into *E. coli* strain HB101 and selected for growth on bacterial plates containing the antibiotic chloramphenicol. Plasmid DNA from individual colonies was analyzed for inserts containing multiple (AB)$_2$ DNA fragments by digestion with FokI REN. Several clones were obtained ranging from one copy to several copies of (AB)$_2$. One clone, pPT 0169, containing (AB)$_6$ was used as an intermediate for the construction of the SequenceD 3 gene monomer.

The (AB)$_6$ gene fragment was purified from pPT 0169 by digestion with FokI REN, agarose gel electrophoresis and NACS purification. This DNA fragment was then ligated with DNA plasmid pPT 0140 that had been previously digested with BanI REN. The products of the ligation were transformed into *E. coli* strain HB101, and transformants were selected on bacterial plates containing the antibiotic chloramphenicol. Plasmid DNA from individual colonies was analyzed by digestion with FokI REN for inserts containing multiple copies of the (AB)$_6$ gene fragment. One clone, pPT 0171, containing C$_2$(AB)$_{12}$C$_2$ (shown in Table 7) was chosen as the SequenceD 3 gene monomer for subsequent constructions.

```
GGTGCTCACGGCCCAGCAGGTCCGAAGGGCGCGCATGGCCCAGCAGGCCCGAAA
CCACGAGTGCCGGGTCGTCCAGGCTTCCCGCGCGTACCGGGTCGTCCGGGCTTT
GAHGPAGPKGAHGPAGPK

⎡ GGTGCTCCGGGACCTGCAGGCCCACCGGGTAGCCGTGGCGATCCGGGACCACCG
 ⎢ CCACGAGGCCCTGGACGTCCGGGTGGCCCATCGGCACCGCTAGGCCCTGGTGGC
 ⎣ G   A   P   G   P   A   G   P   P   G   S   R   G   D   P   G   P   P

Xba
I
GGTGCACCTGGCCCAGCGGGTCCGCCTGGATCTAGAGGTGACCCAGGACCGCCT   ⎤
CCACGTGGACCGGGTCGCCCAGGCGGACCTAGATCTCCACTGGGTCCTGGCGGA   ⎥
G   A   P   G   P   A   G   P   P   G   S   R   G   D   P   G   P   ⎦6

Ban
I
GGTGCCCATGGCCCAGCAGGACCGAAAGGAGCTCACGGTCCGGCAGGTCCGAAA
                                                   SEQ ID NO:46

CCACGGGTACCGGGTCGTCCTGGCTTTCCTCGAGTGCCAGGCCGTCCAGGCTTT
                                                   SEQ ID NO:47

GAHGPAGPKGAHGPAGPK
```

SequenceD 3 Polymer Gene Construction

Plasmid DNA from pPT 0171 was digested with FokI REN and the fragment containing the DCP 3 gene monomer purified by agarose gel electrophoresis and NACS purification. The SequenceD 3 monomer was then self-ligated and then ligated with DNA plasmid pSY 1262 that had been digested with BanI REN. The products of the ligation were transformed into E. coli strain HB101 and selected for growth on bacterial plates containing the antibiotic kanamycin. Plasmid DNA from individual colonies was purified and analyzed after digestion with XcmI and PvuII RENs for insertions containing multiple copies of the DCP 3 gene monomer fragment. Clones pPT 0173, pPT 0174, pPT 0175 and pPT 0176 containing monomer, dimer, trimer and tetramer forms of SequenceD 3, respectively, were selected for expression analysis.

SequenceD 3 Protein Expression Analysis.

E. coli strain HB101 containing SequenceD 3 plasmids pPT 0173, pPT 0174, pPT 0175, or pPT 0176 were grown at 30° C. to an OD$_{600}$ of 0.7 and then shifted to 42° C. for 2.0 hours. The proteins produced by these cells were analyzed by western blot analysis for novel protein bands reactive with SequenceD-(AB)$_2$ peptide specific antisera. Reactive bands were observed with each clone (see Table 8 for results). However, the expression of the full length polymer decreased with the increased size of the genes. Northern analysis using the SequenceD3 monomer as a probe showed that the synthesis of full length mRNA in these clones was at equivalent levels.

TABLE 8

| Sequence D 3 Expression clones | # of repeats | Gene size (in bp) | # of amino acids | Protein band observed (in kD) |
|---|---|---|---|---|
| pPT 0173 | 1 | 927 | 309 | 28 |
| pPT 0174 | 2 | 1683 | 561 | 64 |
| pPT 0175 | 3 | 2439 | 813 | 98 |
| pPT 0176 | 4 | 3195 | 1065 | 135 |

Sequence 3 pPT 0176 1065 Amino Acids MW: 91,966 Dalton
MDPVVLQRRDWENPGVTQLNRLAAHPPFASDPM
{(GAHGPAGPK)$_2$ [(GAPGPAGPP)(GSRGDPGPP)]$_{12}$ (GAHGPAGPK)$_2$}$_4$
GAMDPGRYQLSAGRYHQLVWCQK SEQ ID No: 48

Example 3

TABLE 9

| STRUCTURE OF SEQUENCE D 4, 5 & 6 | |
|---|---|
| SEQUENCE D4 | [C$_2$(DB)$_{12}$C$_2$]$_4$ |
| SEQUENCE D5 | [C$_2$(DB)$_6$C$_2$]$_4$ |
| SEQUENCE D6 | [C$_2$D$_{24}$C$_2$]$_4$ |
| where: | |
| B = GSRGDPGPP SEQ ID NO:49 | |
| C = GAHGPAGPK SEQ ID NO:50 | |
| D = GAQGPAGPG SEQ ID NO:51 | |

SequenceD 4 and 5 Gene Monomer Constructions

Three double stranded DNA sections, coding for (DB)$_3$, were synthesized, purified and annealed as described in Example 1.

```
                                          Eco0109I                                              5.A)
                                        SEQ ID NO:52
5'-GTGCACAGGGACCGGCGGGACCAGGTGGCTCTCGAGGCGATCCGGGTCCTCCGG

SEQ ID NO:53                                 5.B)
3'-       TGTCCCTGGCCGCCCTGGTCCACCGAGAGCTCCGCTAGGCCCAGGAGGCCCACG

Eco0109I                            DraIII                                       5.C)
                                                 SEQ ID NO:54
5'-GTGCACAAGGACCGGCAGGCCCTGGTGGCAGCCGCGGTGATCCGGGCCCACCGG

SEQ ID NO:55                                 5.D)
3'-       TGTTCCTGGCCGTCCGGGACCACCGTCGGCGCCACTAGGCCCGGGTGGCCCACG

SEQ ID NO:56                                 5.E)
5'-GTGCTCAAGGACCGGCTGGCCCAGGCGGTTCCCGTGGAGACCCGGGTCCACCGG

SEQ ID NO:57                                 5.F)
3'-       AGTTCCTGGCCGACCGGGTCCGCCAAGGGCACCTCTGGGCCCAGGTGGCCCACG
```

The three DNA sections were cloned separately. The first two strand section (5.A & 5.B) was ligated to pPT 0138 previously digested with BanI REN. The ligation products were transformed into *E. coli* strain HB101 and selected for growth on bacterial plates containing the antibiotic chloramphenicol. Plasmid DNA from individual colonies was digested with Eco0109I and StuI RENs and analyzed by agarose gel electrophoresis. Plasmid DNA containing an appropriately sized DNA fragment was sequenced and one clone, pPT 0221, was used in subsequent constructions.

in Table 10, containing the desired sequence was used in the subsequent constructions of the SequenceD 4 and SequenceD 5 monomers.

TABLE 10

```
GGT GCA CAG GGA CCG GCG GGA CCA GGT GGC TCT CGA GGC GAT CCG GGT CCT CCG
CCA CGT GTC CCT GGC CGC CCT GGT CCA CCG AGA GCT CCG CTA GGC CCA GGA GGC
 G   A   Q   G   P   A   G   P   G   G   S   R   G   D   P   G   P   P

GGT GCA CAA GGA CCG GCA GGC CCT GGT GGC AGC CGC GGT GAT CCG GGC CCA CCG
CCA CGT GTT CCT GGC CGT CCG GGA CCA CCG TCG GCG CCA CTA GGC CCG GGT GGC
 G   A   Q   G   P   A   G   P   G   G   S   R   G   D   P   G   P   P

GGT GCT CAA GGA CCG GCT GGC CCA GGC GGT TCC CGT GGA GAC CCG GGT CCA CCG   SEQ ID NO: 58
CCA CGA GTT CCT GGC CGA CCG GGT CCG CCA AGG GCA CCT CTG GGC CCA GGT GGC
 G   A   Q   G   P   A   G   P   G   G   S   R   G   D   P   G   P   P   SEQ ID NO: 59
```

The second pair of oligonucleotide strands (5.C & 5.D) were ligated with pPT 0134 which had been digested with FokI REN. After transformation of *E. coli*, plasmid DNA from individual colonies was analyzed by digestion with BanII and StuI RENs. DNAs that were digested by both enzymes were sequenced. One clone, pPT 0222, had the expected sequence and was used for subsequent constructions.

Plasmid DNA from pPT 0222 was digested with FokI REN and the fragment (54 bp) containing the second pair of oligonucleotide strands (5C & 5D) was isolated by agarose gel electrophoresis followed by NACS purification. This DNA fragment was ligated with pPT 0221 previously digested with BanI REN. The products of the ligation were transformed into *E. coli* and plasmid DNA from single colonies was analyzed by agarose gel electrophoresis after digestion with DraIII and StuI RENs. One clone, pPT 0223, was chosen, after DNA sequencing, to be the acceptor vector for the third synthesized SequenceD gene fragment.

Plasmid pPT 0223 was digested with BanI REN and ligated with the third pair of oligonucleotides (5.E & 5.F). The product of the ligation reactions was transformed into *E. coli* strain HB101 and selected for growth on bacterial plates containing the antibiotic chloramphenicol. Plasmid DNA from individual transformants was purified and digested with FokI and BanI RENs. Clones containing the correct fragment size were sequenced. One clone, pPT0224, shown Plasmid DNA from pPT 0224 was digested with FokI and BanI RENs and the digestion fragment carrying (DB)$_3$ was isolated by agarose gel electrophoresis and purified on a NACS column. The purified fragment was self-ligated and then cloned into pPT 0140 which had been digested with BanI REN. The products of the ligation were transformed into *E. coli* strain HB 101. Plasmid DNA from individual colonies was analyzed for inserts containing multiple (DB)$_3$ DNA fragments by digestion with FokI. Several size inserts were found ranging from (DB)$_3$ to (DB)$_{12}$. One clone, pPT 0229, was identified to contain the desired SequenceD 5 monomer sequence, C$_2$(DB)$_6$C$_2$, and was used for subsequent constructions. The clone containing the SequenceD 4 gene monomer sequence C$_2$(DB)$_{12}$C$_2$ was found to be highly unstable during subsequent passages, as was observed during the construction of SequenceD 1. Subsequently, a new plasmid was constructed to use as an acceptor for the SequenceD 4 gene monomer fragment.

Plasmid pACYC 184 (Chang and Cohen, J. Bacteriol. 134, 1141–1156 [1977]) was digested with BanI REN, purified by agarose gel electrophoresis, and the DNA fragment corresponding to approximately 2000 bp was further purified using a NACS column. This DNA fragment was filled in using DNA polymerase (see Example 1) and then self-ligated. The products of the ligation mixture were transformed into *E. coli* strain HB101 and selected on bacterial plates containing chloramphenicol at 30 μg/ml. Plasmid DNA from individual colonies was linearized by digestion with Eco47III. One clone, pPT 0235, was used as the acceptor vector for the SequenceD 4 monomer.

The plasmid DNA containing the SequenceD 4 gene monomer fragment was isolated from the plasmid by digestion with DraI and PvuII RENs, followed by agarose gel electrophoresis. The agarose slice containing the DCP 4 gene monomer fragment was ligated with plasmid pPT 0235 previously digested with Eco47III REN, and purified by agarose gel electrophoresis and NACS column. The products of this ligation were transformed into *E. coli* strain HB101 and selected on bacterial plates containing chloramphenicol at 30 µg/ml. Plasmid DNA from individual colonies was analyzed by digestion with NruI and EcoRV RENs. One clone containing the SequenceD 4 gene monomer fragment, pPT 0237, was chosen for the construction of the SequenceD 4 polymer gene. This plasmid was stably maintained in *E. coli*.

SequenceD 4 Polymer Gene Construction

Plasmid DNA from pPT 0237 was digested with FokI REN. The DNA fragment containing the SequenceD 4 gene monomer was isolated by agarose gel electrophoresis and purified using a NACS column (see Example 1). The monomer gene fragment was then ligated with pSY 1262 which had been previously digested with BanI REN, treated with phosphatase, and purified by gel electrophoresis and NACS column. The ligation products were transformed into *E. coli* strain HB101 and the transformants were selected for growth on bacterial plates containing the antibiotic kanamycin at 50 µg/ml. Plasmid DNA from individual colonies was purified and analyzed for multiple insertion of the SequenceD 4 gene monomer fragment. Several clones were obtained containing one, two or four copies of the SequenceD 4 gene monomer. Plasmids pPT0247, pPT0248, and pPT0249 containing respectively 1, 2, and 4 copies of the gene monomer, were selected for protein expression analysis.

SequenceD 4 Protein Expression Analysis

*E. coli* strain HB101 containing plasmids pPT 0247, pPT 0248, and pPT 0249 were grown at 30° C. to an $OD_{600}$ of 0.7 and then shifted to 42° C. for 2.0 hours. The proteins produced by these cells were analyzed by western blot analysis for novel protein bands reactive with DCP-$C_2(A_2)$ peptide specific antisera. A reactive band corresponding to full length product was observed with each clone.

Sequence D 4   pPT 0249   1065 Amino Acids   MW: 91,533 Dalton
MDPVVLQRRDWENPGVTQLNRLAAHPPFASDPM
$\{(GAHGPAGPK)_2\ [(GAQGPAGPG)(GSRGDPGPP)]_{12}\ (GAHGPAGPK)_2\}_4$
GAMDPGRYQLSAGRYHYQLVWCCK SEQ ID NO: 60

SequenceD 5 Polymer Gene Construction

Plasmid DNA from pPT 0229 containing the SequenceD 5 gene monomer was isolated after digestion with FokI REN by agarose gel electrophoresis followed by NACS purification. The gene fragment was ligated with pSY 1262 which had been digested with BanI REN. The products of the ligation were transformed into *E. coli* strain HB101 and selected for growth on bacterial plates containing the antibiotic kanamycin at 50 μg/ml. Plasmid DNA from individual colonies was purified and analyzed for inserts containing multiple copies of the SequenceD 5 gene monomer sequence $C_2(DB)_6C_2$. Plasmids pPT 0231 and pPT 0232, respectively, contained three and four copies of the SequenceD 5 gene monomer and were used for expression analysis.

SequenceD 5 Protein Expression Analysis

*E. coli* strain HB101 containing plasmids pPT 0231 and pPT 0232 were grown at 30° C. to an $OD_{600}$ of 0.7 and then shifted to 42° C. for 2.0 hours. The proteins produced by these cells were analyzed by western blot analysis for novel protein bands reactive with SequenceD-$C_2A_2$ peptide specific antisera. A reactive band corresponding to full length product was observed with each clone.

Sequence D 5 pPT0232 633 Amino Acids MW: 55,228 Daltons
MDPVVLQRRDWENPGVTQLNRLAAHPPFASDPM
$\{(GAHGPAGPK)_2\ [(GAQGPAGPG)(GSRGDPGPP)]_6\ (GAHGPAGPK)_2\}_4$
GAMDPGRYQLSAGRYHYQLVWCQK SEQ ID NO: 61

SequenceD 6 Gene Monomer Construction

Four oligonucleotide strands encoding $D_4$, were synthesized, purified and annealed as described in Example 1.

EcoO109I 6.A)
5'-GTGCACAGGGACCGGCGGGTCCAGGCGGTGCTCAAGGACCGGCAGGCCCTTAATTAAG SEQ ID NO: 62

3'- TGTCCCTGGCCGCCCAGGTCCGCCACGAGTTCCTGGCCGTCCGGGAATTAATT- 6.B)
CCACG SEQ ID NO: 63

(EcoO109I) 6.C)
5'-GCCCTGGTGGCGCTCAAGGTCCGGCTGGCCCAGGAGGCGCGCAGGGTCCGGCAGGT-

3'- GACCACCGCGAGTTCCAGGCCGACCGGGTCCTCCGCGCGTCCCAGGCCGTCCA- 6.D)
CCGGGAG SEQ ID NO: 64
GGCCCTCCACG SEQ ID NO: 65

The first oligonucleotide segment consisting of strands 6A and 6B was ligated to pPT 0138 previously digested with BanI REN. The ligation products were transformed into *E. coli* strain HB101 and selected for growth on bacterial plates containing the antibiotic chloramphenicol. Plasmid DNA from individual colonies was digested with EcoO109I and XmnI RENs and analyzed by agarose gel electrophoresis. Plasmid DNA containing the correct sized fragment was sequenced and one clone, pPT 0219, containing the correct sequence was used for subsequent constructions.

Plasmid pPT 0219 was digested with BanI and Eco0109I RENs and ligated with the second pair of oligonucleotides (6C and 6D). The products of the ligation were transformed into *E. coli* strain HB101 and selected for growth on bacterial plates containing the antibiotic chloramphenicol. Plasmid DNA from transformants was purified and digested with FokI and BanI RENs. Clones containing the correct fragment size were sequenced. One clone, pPT 0220, containing the sequence shown in Table 11 was used in subsequent constructions of the SequenceD 6 gene monomer.

Properties of Purified SequenceD6

TABLE 11

```
GGTGCACAGGGACCGGCGGGTCCAGGCGGTGCTCAAGGACCGGCAGGCCCTGGT
CCACGTGTCCCTGGCCGCCCAGGTCCGCCACGAGTTCCTGGCCGTCCGGGACCA
  G   A   Q   G   P   A   G   P   G   G   A   Q   G   P   A   G   P   G

GGCGCTCAAGGTCCGGCTGGCCCAGGAGGCGCGCAGGGTCCGGCAGGTCCGGGA     SEQ ID NO:66
CCGCGAGTTCCAGGCCGACCGGGTCCTCCGCGCGTCCCAGGCCGTCCAGGCCCT
  G   A   Q   G   P   A   G   P   G   G   A   Q   G   P   A   G   P   G        SEQ ID NO:67
```

Plasmid DNA containing the $D_4$ sequence was digested with FokI and BanI RENs and the digestion fragment containing $D_4$ was isolated by agarose gel electrophoresis followed by NACS purification. The purified fragment was self-ligated and subsequently ligated with DNA plasmid pPT 0140 digested with BanI REN. The ligation products were transformed into *E. coli* strain HB101 and selected for growth on bacterial plates containing the antibiotic chloramphenicol. A transformant, pPT 0242, containing the SequenceD 6 gene monomer (($D_4)_6$ flanked by $C_2$-$C_2$) was used for subsequent constructions.

DCP 6 Polymer Gene Construction

Plasmid DNA from pPT 0242 was digested with FokI REN. The DNA fragment containing the SequenceD 6 gene monomer was isolated by agarose gel electrophoresis and purified using a NACS column. The monomer gene fragment was then ligated with pSY 1262 which had been previously digested with BanI REN, treated with phosphatase, and purified by gel electrophoresis and NACS column. The ligation products were transformed into *E. coli* strain HB101 and the transformants were selected for growth on bacterial plates containing the antibiotic kanamycin at 50 µg/ml. Plasmid DNA from individual colonies was purified and analyzed for multiple insertion of the SequenceD 6 gene monomer sequence, $C_2D_{24}C_2$. Several clones were obtained ranging from one to four repeats of the SequenceD 6 gene monomer. Plasmids pPT 0243, pPT 0244, pPT 0245, and pPT 0246 containing respectively 1, 2, 3, and 4 repeats of the gene monomer were selected for protein expression analysis.

Sequence D6 Protein Expression Analysis

*E. coli* strain HB101 containing plasmids pPT 0243 to pPT 0246 were grown at 30° C. to an $OD_{600}$ of 0.7 and then shifted to 42° C. for 2.0 hours. The proteins produced by these cells were analyzed by western blot analysis for novel protein bands reactive with SequenceD-$C_2A_2$ peptide specific antisera. See Table 11 for the results.

TABLE 11

| Sequence D 3 Expression clones | # of repeats | Gene size (in bp) | # of amino acids | Protein band observed (in kD) |
|---|---|---|---|---|
| pPT 0243 | 1 | 927 | 309 | no detection |
| pPT 0244 | 2 | 1683 | 561 | 72 |
| pPT 0245 | 3 | 2439 | 813 | 110 |
| pPT 0246 | 4 | 3195 | 1065 | 140 | pPT 0246 1,065 Amino Acids MW: 85,386 Dalton
MDPVVLQRRDWENPGVTQLNRLAAHPPFASDPM
[(GAHGPAGPK)$_2$ (GAQGPAGPG)$_{24}$ (GAHGPAGPK)$_2$]$_4$
GAMDPGRYQLSAGRYHYQLVWCCK SEQ ID No: 68

The protein polymer, SequenceD6, was purified in multigram quantities as produced from *E. coli* strain pPT 0246 using standard protein purification, extraction, and separation methods. The lyophilized product was a white, spongy material. By amino acid compositional analysis, the product was shown to consist primarily of the amino acids glycine, alanine, proline and glutamine. The molar % glycine+ alanine+ proline out of the total amino acids were 82.8%. The molar ratio of glycine, alanine, proline, and glutamine was 1.95:0.89:1.00:0.89, respectively. The theoretical ratio of these amino acids for SequenceD6 polymer is 1.90:1.00:1.00:0.43.

The purified product was dried and analyzed for elemental composition. The chemical analysis showed the product to contain 50.5% carbon, 6.78% hydrogen, 19.5% nitrogen, 11.3% water and less than 0.1% noncombustible ash. Theoretical elemental composition of SequenceD6 is 50.9% carbon, 6.49% hydrogen and 20.2% nitrogen. These analyses indicate that the dried product consists of approximately 85.7% protein, and that approximately 98.6% of that protein is DCP6.

The dried product is extremely soluble in water. 8% weight solutions or greater can be easily produced. At room temperature or above such solutions are viscous but fluid. Upon chilling to 0° C. the solution forms a solid gel which does not flow and is semi-transparent. Upon heating to greater than 28° C., the gel forms a thick solution. This thermoreversible transition between the liquid and gel phases of the polymer solution can occur repeatedly with no apparent physical change in the polymer structure.

Plasmid pPT 0285 Construction

Two oligonucleotide strands were synthesized and purified as described in Example 1:

```
                    (Eco47III)PmeI    PmlI    NruI      BanI
StuI EcoRV SnaBI(SnaI)
1. 5'-   GCTATGTTTAAACCACGTGTTCGCGATCCGGGTGCCGATCCAGGCCTGCGATATCA-
2. 3'-   CGATACAAATTTGGTGCACAAGCGCTAGGCCCACGGCTAGGTCCGGACGCTATAGT-
         A   M   F   K   P   R   V   R   D   P   G   A   D   P   G   L   R   Y   Q
         (5' [continued])  GTACGTA    SEQ ID NO: 69
         (3' [continued])  CATGCAT
                           Y    V
```

The two oligonucleotide strands were annealed and ligated with the DNA of plasmid pPT 0235 which had been digested with Eco47III and SnaI RENs.

The product of this ligation reaction was transformed into *E. coli* strain HB101. Plasmid DNA from transformants was purified and digested with EcoRI in combination with Eco47III or SnaI or NruI RENs. Plasmid DNA from two clones that gave the correct digestion pattern was sequenced. One plasmid, designated pPT 0285, was found to be correct and chosen for further constructions.

CLP 3.1 Gene Monomer Construction

The CLP 3.1 synthetic gene was assembled from smaller parts. First, four double-stranded sections of DNA were chemically synthesized.

Fragment 1, after annealing, was digested with PstI REN; the digestion mixture was treated with a BioSpin column as was the phosphorylated fragment 3 strands. All four fragments were then loaded on a 12% polyacrylamide gel in 0.5×TBE and the bands corresponding to double stranded DNA were identified by UV shadowing, excised from the gel and extracted by the crush and soak procedure (Smith, Methods in Enzymology, 65, 371–379 [1980]).

The fragments were then ligated into pPT 0285 previously digested with BanI and EcoRV RENs and further purified by NACS column (see Example 1). The product of the ligation reaction was transformed into *E. coli* strain HB101. Plasmid DNA from transformants was purified and digested with PvuII and SacII; clones containing inserts of the correct size

```
FRAGMENT 1:
   BanI                                                      PstI         BanII      BanI
5'- GTGCCCCTGGCGCTCCGGGTTCTCAAGGTGCACCGGGTCTGCAGAAAGGGCTCTTTCACCGG  SEQ ID NO: 70
3'-        GGGACCGCGAGGCCCAAGAGTTCCACGTGGCCCAGACGTCTTTCCCGAGCCACG   SEQ ID NO: 71

FRAGMENT 2:
   PstI                                                      BanIII
5'-     GGGTGCACCGGGAGCGCCAGGTAGCCAGGGTGCACCGGGATTGCAGGGGGCT  SEQ ID NO: 72
3'- ACGTCCCACGTGGCCCTCGCGGTCCATCGGTCCCACGTGGCCCTAACGTCCC     SEQ ID NO: 73

FRAGMENT 3:
   BanII                                                     DraIII
5'-  CCGGGTGCACCAGGTAGCCAGGGAGCACCGGGTCTGCAAGGAGCACCGG  SEQ ID NO: 74
3'-CCGAGGCCCAGCTGGTCCATCGGTCCCTCGTCCGCCAGACGTTCCTCGTG   SEQ ID NO: 75

FRAGMENT 4:
       DraIII      BamHI                                             BanI    StuI  EcoRV
5'-       CAAACACCGGGTGCACCGGGATCCCAGGGCGCTCCGGGCCTGCAAGGTGCCAGGCCTCGAT  SEQ ID NO: 76
3'-CCGAGTTTGTGGCCCACGTGGCCCTAGGGTCCCGGCAGGCCCGGACGTTCCACGGTCCGGAGCAT    SEQ ID NO 77
```

The two strands of fragment 3 were phosphorylated before annealing using Polynucleotide Kinase 3'-phosphatase-free (see Example 1). All of the fragments were then individually annealed using the procedure described in Example 1.

were further analyzed with EcoRI in combination with several restriction endonucleases to determine the presence of unique restriction endonuclease sites prior to sequencing. One clone looked promising and was sequenced. Plasmid pPT 0291 contained the sequence shown in Table 12, containing all four fragments, but had a deletion of 17 bases in fragment 3 including the DraIII restriction site.

TABLE 12

```
     Ban I                                          Pst I
5'- GGT GCC CCT GGC GCT CCG GGT TCT CAA GGT GCA CCG GGT CTG CAG
    CCA CGG GGA CCG CGA GGC CCA AGA GTT CCA CGT GGC CCA GAC GTC
     G   A   P   G   A   P   G   S   Q   G   A   P   G   L   Q

GGT GCA CCG GGA GCG CCA GGT AGC CAG GGT GCA CCG GGA TTG CAG
    CCA CGT GGC CCT CGC GGT CCA TCG GTC CCA CGT GGC CCT AAC GTC
     G   A   P   G   A   P   G   S   Q   G   A   P   G   L   Q

Ban II
    GGG GCT CCG GGT GCA CCA GGT AGC CAG GGA GCA CCG GGT
    CCC CGA GGC CCA CGT GGT CCA TCG GTC CCT CGT GGC CCA
     G   A   P   G   A   P   G   S   Q   G   A   P   G

Bam HI                     Ban I
    T GCA CCG GGA TCC CAG GGC GCT CCG GGC CTG CAA GGT GCC   SEQ ID NO:78
    A CGT GGC CCT AGG GTC CCGCGA  GGC CCG GAC GTT CCA CGG
       A   P   G   S   Q   G   A   P   G   L   Q           SEQ ID NO:79
```

This plasmid was used to construct the CLP 3.1 monomer. Fragment 3 was ligated with fragment 4 using the HCC ligation method, see Example 1. The product of the ligation mixture was electrophoresed in 2% low melting agarose gel and the band corresponding to the ligated product was excised from the gel and ligated with pPT 0291 plasmid DNA that had been previously digested with BanII and SnaBI RENs and purified by agarose gel electrophoresis and NACS column.

The product of the ligation reaction was transformed into *E. coli* strain HB101. Plasmid DNA from transformants was purified and digested with BamHI and EcoRI RENs; clones that showed the correct restriction pattern were further analyzed with BanII or DraIII RENs; three clones containing inserts of the correct size were sequenced. Plasmid pPT 0292 contained the desired CLP 3.1 monomer sequence (see Table 13).

transferred to a new flask prewarmed at 42° C. and incubated at the same temperature for approximately 2 hours. The cultures (30° and 42°) were chilled on ice and $OD_{600}$ was taken. Cells were collected by centrifugation and divided into 1.0 $OD_{600}$ aliquots which were then used to perform dot blot and western blot analysis using CLP 3.1 peptide specific antisera (see Example 1). See Table 14 for the results. For purification and amino acids analysis larger cultures were used.

TABLE 14

| CLP 3.1 Expression clones | # of repeats | Gene size (in bp) | # of AA | Protein bands observed (in kD) |
| --- | --- | --- | --- | --- |
| pPT 0293 | 6 | 1251 | 417 | 45 |
| pPT 0294 | 9 | 1791 | 597 | 65 |

TABLE 13

```
      Ban I
5'- GGT GCC CCT GGC GCT CCG GGT TCT CAA GGT GCA CCG GGT CTG CAG
    CCA CGG GGA CCG CGA GGC CCA AGA GTT CCA CGT GGC CCA GAC GTC
    G   A   P   G   A   P   G   S   Q   G   A   P   G   L   Q

GGT GCA CCG GGA GCG CCA GGT AGC CAG GGT GCA CCG GGA TTG CAG
    CCA CGT GGC CCT CGC GGT CCA TCG GTC CCA CGT GGC CCT AAC GTC
    G   A   P   G   A   P   G   S   Q   G   A   P   G   L   Q

Ban II
    GGG GCT CCG GGT GCA CCA GGT AGC CAG GGA GCA CCG GGT CTG CAA
    CCC CGA GGC CCA CGT GGT CCA TCG GTC CCT CGT GGC CCA GAC GTT
    G   A   P   G   A   P   G   S   Q   G   A   P   G   L   Q

Dra III         Bam HI                    Ban I
    GGA GCA CCG GGT GCA CCG GGA TCC CAG GGC GTC CCG GGC CTG CAA GGT
    CCT CGT GGC CCA CGT GGC CCT AGG GTC CCG CGA GGC CCG GAC GTT CCA
        G   A   P   G   A   P   G   Q   G   A   P   G   L   Q   SEQ ID NO:81

GCC
CGG    SEQ ID NO:80
```

CLP 3.1 Polymer Gene Construction

Plasmid DNA pSY 1262 was digested with BanI REN. The digestion mixture was divided into two aliquots. One was treated with Calf Intestinal Phosphatase and the other was treated with Shrimp Alkaline Phosphatase (SAP), as described in Example 1.

Plasmid DNA from pPT 0292 was digested with BanI REN and the digestion fragments were separated by agarose gel electrophoresis. The CLP 3.1 gene fragment, 180 bp, was excised and purified by NACS column (see Example 1) and then ligated with plasmid pSY 1262 prepared as described above.

The product of this ligation reaction was transformed into *E. coli* strain HB101. Transformants were selected for resistance to kanamycin. Plasmid DNA from individual transformants was purified and analyzed for increase size due to CLP 3.1 multiple DNA insertion. Several clones were obtained ranging in size from approximately 1.0 kbp to 3.0 kbp. Five clones, pPT 0293 to pPT 0297, containing respectively 6, 9, 11, 13, and 17 repeats of the gene monomer were selected for protein expression analysis.

CLP 3.1 Protein Expression Analysis

Overnight cultures of *E. coli* strain HB101 containing plasmids pPT 0293 to pPT 0297 which had been grown at 30° C. were separately used to inoculate 50 ml of media contained in a 250 ml flask. Kanamycin was added at a final concentration of 50 μg per ml and the cultures were incubated with agitation (200 rpm) at 30° C. When the cultures reached an $OD_{600}$ of 0.8, 40 ml of each culture were TABLE 14-continued

| CLP 3.1 Expression clones | # of repeats | Gene size (in bp) | # of AA | Protein bands observed (in kD) |
| --- | --- | --- | --- | --- |
| pPT 0295 | 11 | 2151 | 717 | 75 |
| pPT 0296 | 13 | 2511 | 837 | 90 |
| pPT 0297 | 17 | 3231 | 1077 | 130 |

*E. coli* strain HB101 containing plasmids pPT 0293 to pPT 0297 were grown as described above. The proteins produced by these cells were analyzed by SDS-PAGE for detection of reactivity to CLP 3.1 peptide specific antisera. In every analysis a strong reactive band was observed of an apparent molecular weight from 45 kD to 130 kD respectively.

pPT 0297    1077 Amino acids    MW: 91,266 Daltons

MDPVVLQRRDWENPGVTQLNRLAAHPPFASDPM
(GAPGAPGSQGAPGLQ)$_{68}$
GAMDPGRYQLSAGRYHYQLWVCQK SEQ ID NO: 82

As evidenced by the above results, high molecular weight collagen-like polymers can be produced. The polymers are characterized by having repeating triads with the first amino acid of each triad being glycine. By lowering the percentage of prolines as compared to natural collagen, a variety of useful collagen-like polymers are formed having properties similar to collagen, but enjoying unique characteristics. The products find use as films, fibers, molded objects, admixed with other natural or synthetic polymers or coatings on fibers, films, labware or other surfaces, e.g., prosthetic devices, and the like.

All publications and patent applications mentioned in this specification are indicative of the level of skill of those skilled in the art to which this invention pertains. All publications and patent applications are herein incorporated by reference to the same extent as if each individual publication or patent application was specifically and individually indicted to be incorporated by reference.

Although the foregoing invention has been described in some detail by way of illustration and example for purposes of clarity of understanding, it will be understood that certain changes and modifications may be practiced within the scope of the appended claims.

What is claimed is:

1. A collagen like polymer of at least about 30 kD, characterized by:
being expressed in a unicellular organism from a construct prepared in vitro;
comprising at least 80 weight % of triads having glycine as the first amino acid and at least 40 number % of said triads comprising at least one proline, wherein the total proline content of said triads is less than 45 number %; and
comprising at least two repetitive units of (glyXO)$_n$, wherein X and O symbolize individual amino acids, X and O are the same or different amino acids in each triad and n is at least 4; wherein at least two triads are selected from the group consisting of the triads gly-ala-pro, gly-pro-ala, gly-pro-pro, gly-ala-ser, gly-pro-gly, gly-pro-ser, gly-ala-gln, gly-ser-pro, gly-ser-gln, gly-leu-gln, gly-pro-arg, gly-pro-lys, gly-ala-lys, gly-ala-arg, gly-glu-arg, gly-asp-arg, gly-glu-pro, gly-asp-ala, gly-ala-his and gly-glu-ala.

2. A collagen like polymer according to claim 1, wherein said polymer comprises at least 15 number % proline of the amino acids and is not more than about 100 kD.

3. A collagen like polymer according to claim 1, wherein X and O are selected from the group consisting of alanine, isoleucine, valine, leucine, serine, threonine, asparagine, glutamine, lysine, arginine, aspartic acid, glutamic acid, histidine and proline.

4. A collagen like polymer according to claim 3, wherein the number of triads comprising proline are at least 60 number %.

5. A collagen like polymer according to claim 1, wherein at least two triads are selected from the group consisting of the triads gly-ala-pro, gly-pro-ala, gly-pro-pro, gly-ala-ser, gly-pro-gly, gly-pro-ser, gly-ala-gln, gly-ser-pro, gly-ser-gln, gly-leu-gln and gly-ala-his.

6. A collagen like polymer according to claim 1, wherein X and O are selected from the group consisting of alanine, isoleucine, valine, leucine, serine, threonine, asparagine, glutamine, histidine and proline.

7. A collagen like polymer of at least about 30 kD, characterized by:
being expressed in a unicellular organism from a construct prepared in vitro;
comprising at least 80 weight % of triads having glycine as the first amino acid and at least 40 number % of said triads comprising at least one proline and the proline total content of said triads is less than 45 number %; and
comprising at least two repetitive units of the formula $\alpha_2\beta_n\alpha_2$, wherein $\alpha$ has three triads characterized as having glycine as the first amino acid and at least two of the triads having a proline; $\beta$ has from three to nine triads, wherein at least 30% of the triads have proline; and n is at least 6 and not more than about 36.

8. A collagen like polymer according to claim 7, wherein $\alpha$ comprises at least one of gly-pro-ala and gly-pro-lys, and $\beta$ comprises at least two of gly-ala-pro, gly-pro-ala, gly-pro-pro, gly-pro-gly, gly-ala-ser or gly-asp-pro.

9. A collagen like polymer according to claim 8, wherein $\beta$ comprises, in one letter amino acid abbreviation, GAPGPAGPP SEQ ID:NO 19, GAPGPAGPPGSRGDPGPP SEQ ID:NO 83, GAQGPAGPGGSRGDPGPP SEQ ID:NO 84, or GAQGPAGPG SEQ ID:NO 85.

10. A collagen like polymer according to claim 7, wherein said polymer comprises at least four repetitive units.

11. A DNA sequence encoding a collagen like polymer according to claim 1.

12. A DNA sequence encoding a collagen like polymer according to claim 7.

13. A unicellular microorganism comprising a DNA sequence encoding a collagen like polymer of at least about 30 kD and fewer than 45 number % proline said DNA sequence being characterized by:
being expressed in said unicellular organism from a construct prepared in vitro; and
comprising at least 80 weight % of triads having glycine as the first amino acid and at least 40 number % of said triads comprising at least one proline and the total proline content of said triads is less than 45 number %; and comprising at least two repetitive units of (glyXO)$_n$, wherein X and O are amino acids and are the same or different in each triad and n is at least 4.

14. A DNA sequence comprising a gene encoding a collagen like polymer of at least about 30 kD, characterized by:

capable of being expressed in a unicellular organism from a construct prepared in vitro;

comprising at least 80 weight % of triads having glycine as the first amino acid; and comprising at least two repetitive units of $(glyXO)_n$, wherein X and O are the same or different in each triad and n is at least 6 where X and O are selected to have from 15 to 45 number percent proline in said polymer;

a transcriptional initiation regulatory region functional in a unicellular microorganism 5' of said gene; and a transcriptional termination regulatory region functional in a unicellular microorganism 3' of said gene;

wherein said gene is under the transcriptional regulation of said regulatory regions.

15. A DNA sequence according to claim 14, wherein said gene encodes a collagen like polymer comprising at least one repeat of a sequence of the following formula:

$$((glyXO)_n \Omega)_m$$

wherein:

X and O are any amino acids, except that X and O are selected to have a proline content of the sequence of at least about 10 and less than about 45 number %;

$\Omega$ has from 0 to 50 amino acids and is other than repetitive glyXO;

n is in the range of 4 to 100; and m is at least one.

16. A DNA sequence according to claim 14, wherein said gene encodes a collagen like polymer of the formula:

$$J^1{}_r(((glyU^u\Pi^\pi)_{p2}(glyX^xO^o)_{n1}(glyU^u\Pi^\pi)_{p2}\Omega^\Omega)_{m1})J^2{}_r$$

wherein:

$J^1$ and $J^2$ are the same or different and are amino acid sequences of from about 1 to 50 amino acids;

X and O are any amino acids except that X and O are selected to have a proline content of the polymer of at least about 30 and less than about 45 number %;

$\Omega$ is an amino acid sequence of 0 to 50 amino acids;

x and o indicate the X and O in each triad may be the same or different;

$\Omega$ indicates that the amino acid sequence in each $\Omega$ may be the same or different;

U and $\Pi$ are any amino acids;

u and $\pi$ indicate the same or different amino acids in the individual triads;

$n^1$ is in the range of about 4 to 75;

the r's are the same or different and are 0 or 1;

$p^2$ is in the range of 0 to 6; and $m^1$ is in the range of about 1 to 20.

17. A method for producing a collagen like polymer of at least about 30 kD, characterized by:

being expressed in a unicellular organism from a construct prepared in vitro;

comprising at least 80 weight % of triads having glycine as the first amino acid; and comprising at least two repetitive units of $(glyXO)_n$, wherein X and O are the same or different in each triad and n is at least 6 where X and O are selected to have from 35 to 45 number percent proline in said polymer;

said method comprising:

growing a unicellular microorganism comprising a DNA sequence according to claim 11 for sufficient time for said gene to be expressed; and isolating said collagen like polymer.

18. A formed object comprising a collagen like polymer of at least about 30 kD, characterized by:

being expressed in a unicellular organism from a construct prepared in vitro;

comprising at least 80 weight % of triads having glycine as the first amino acid; and comprising at least two repetitive units of $(glyXO)_n$, wherein X and O are the same or different in each triad and n is at least 4 wherein X and O are selected to have from about 10 to 45 number % proline in said polymer.

19. A formed object according to claim 18, wherein said formed object is a gel, film or fiber.

20. An antibody composition prepared in response to a collagen like polymer according to claim 1 or fragment of said collagen like polymer.

21. An antibody composition according to claim 20, wherein said antibody composition is a monoclonal antibody composition.

* * * * *

UNITED STATES PATENT AND TRADEMARK OFFICE
CERTIFICATE OF CORRECTION

PATENT NO. : 5,496,712
DATED : March 5, 1996
INVENTOR(S) : Joseph Cappello; Franco A. Ferrari It is certified that error appears in the above-indentified patent and that said Letters Patent is hereby corrected as shown below:

Col. 3, line 63, change "GXO" to --X and O--.
Col. 4, line 12, change "$((GX^1O^1)(GX^2O^2)(GX^3O^3))_nl$" to --$((glyX^1O^1)(glyX^2O^2)(glyX^3O^3))_nl$--.
Col. 4, line 45, change "$(glyU^u\Omega^\pi)_p(glyX^xO^o)_nl(glyU^u\Omega^\pi)_pl\Omega^\Omega)_ml$" to --$(glyU^u\Pi^\pi)_p(glyX^xO^o)_nl(glyU^u\Pi^\pi)_pl\Omega^\Omega)_ml$--.
Col. 4, line 47, change "$GX^x,O^o,Z^z$" to --$X^x,O^o,\Omega^\Omega$--
Col. 4, line 48, change "U and $\pi$" to --U and $\Pi$--.
Col. 5, line 35, change "$J^1_r(glyU^u\Omega^\pi)_{p2}(glyX^xO^o)_nl(glyU^u\Omega^\pi)_{p2})\Omega^1)_ml)J^2_r$," to --$J^1_r(glyU^u\Pi^\pi)_{p2}(glyX^xO^o)_nl(glyU^u\Pi^\pi)_{p2})\Omega^1)_ml)J^2_r$--.
Col. 8, line 48, change "Mannhaim" to --Mannheim--.
Col. 11, line 32, change "27:80-685(1970)" to --27:680-685(1970)--.
Col. 13, line 67, change "DCP" to --Sequence D--.
Col. 21, line 24, change "DCP" to --Sequence D--.
Col. 24, line 54, change "[1977]" to --[1978]--.
Col. 24, line 67, change "DCP" to --Sequence D--.
Col. 27, line 25, change "DCP" to --Sequence D--.
Col. 28, line 40, change "DCP 6" to --Sequence D--.

Signed and Sealed this

Third Day of December, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,496,712
DATED : March 5, 1996
INVENTOR(S) : Joseph Cappello; Franco A. Ferrari It is certified that error appears in the above-indentified patent and that said Letters Patent is hereby corrected as shown below:

On the cover page of the Patent, please correct the Assignee from "Protein Polymer" to:

--[73] Assignee: Protein Polymer Technologies, Inc.--

Signed and Sealed this

Twenty-eighth Day of October, 1997

Attest:

BRUCE LEHMAN

*Attesting Officer*

*Commissioner of Patents and Trademarks*

SEQUENCE LISTING ( 1 ) GENERAL INFORMATION:

( i i i ) NUMBER OF SEQUENCES: 85

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Gly  Ala  Pro  Gly  Pro  Ala  Gly  Pro  Lys
    1                     5

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Gly  Ala  Pro  Gly  Pro  Ala  Gly  Pro  Pro  Gly  Ala  His
    1                     5                          10

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Gly  Ser  Pro  Gly  Ala  Pro  Gly  Pro  Ala
    1                     5

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Gly  Ala  Pro  Gly  Pro  Ala  Gly  Ser  Arg  Gly  Asp  Pro  Gly  Pro  Ala
    1                     5                          10                               15

( 2 ) INFORMATION FOR SEQ ID NO:5:

( i ) SEQUENCE CHARACTERISTICS:
    ( A ) LENGTH: 18 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:5:

Gly Ala Asn Gly Ala Pro Gly Pro Ala Gly Pro Ala Gly Ala Pro Gly
1               5                   10                  15

Pro Pro ( 2 ) INFORMATION FOR SEQ ID NO:6:

( i ) SEQUENCE CHARACTERISTICS:
    ( A ) LENGTH: 18 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:6:

Gly Ala Gln Gly Pro Ala Gly Pro Gly Gly Ala Pro Gly Pro Ala Gly
1               5                   10                  15

Pro Gly ( 2 ) INFORMATION FOR SEQ ID NO:7:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:7:

Gly Ala Pro Gly Pro Ala Gly Ala Ser
1               5

( 2 ) INFORMATION FOR SEQ ID NO:8:

( i ) SEQUENCE CHARACTERISTICS:
    ( A ) LENGTH: 18 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:8:

Gly Pro Ala Gly Ala Pro Gly Ser Arg Gly Asp Pro Gly Ala Pro Gly
1               5                   10                  15

Pro Pro ( 2 ) INFORMATION FOR SEQ ID NO:9:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:9:

Gly Val Ser Gly Pro Arg Gly Pro Ala Gly Ala Pro Gly Pro Pro
1               5                   10                  15

( 2 ) INFORMATION FOR SEQ ID NO:10:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:10:

Gly Ala Gln Gly Pro Ala Gly Pro Gly
1               5

( 2 ) INFORMATION FOR SEQ ID NO:11:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:11:

Gly Ala His Gly Pro Ala Gly Pro Lys
1               5

( 2 ) INFORMATION FOR SEQ ID NO:12:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:12:

Gly Ala His Gly Pro Ala Gly Pro Arg
1               5

( 2 ) INFORMATION FOR SEQ ID NO:13:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:13:

Gly Ala Val Gly Ala Pro Gly Pro Lys
1               5

( 2 ) INFORMATION FOR SEQ ID NO:14:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:14:

Gly Pro Ala Gly Ala Pro Gly Glu Pro
1               5

( 2 ) INFORMATION FOR SEQ ID NO:15:

( i ) SEQUENCE CHARACTERISTICS:
    ( A ) LENGTH: 9 amino acids (B) TYPE: amino acid
(D) TOPOLOGY: linear (ii) MOLECULE TYPE: peptide (xi) SEQUENCE DESCRIPTION: SEQ ID NO:15:

Gly Val Ser Gly Pro Arg Gly Ala Pro
1               5

(2) INFORMATION FOR SEQ ID NO:16:

(i) SEQUENCE CHARACTERISTICS:
    (A) LENGTH: 36 amino acids
    (B) TYPE: amino acid
    (D) TOPOLOGY: linear (ii) MOLECULE TYPE: peptide (xi) SEQUENCE DESCRIPTION: SEQ ID NO:16:

Gly Ala His Gly Pro Ala Gly Pro Lys Gly Ala His Gly Pro Ala Gly
1               5                   10                  15
Pro Lys Gly Ala Pro Gly Pro Ala Gly Pro Pro Gly Ala Pro Gly Pro
                20                  25                  30
Ala Gly Pro Pro
        35

(2) INFORMATION FOR SEQ ID NO:17:

(i) SEQUENCE CHARACTERISTICS:
    (A) LENGTH: 18 amino acids
    (B) TYPE: amino acid
    (D) TOPOLOGY: linear (ii) MOLECULE TYPE: peptide (xi) SEQUENCE DESCRIPTION: SEQ ID NO:17:

Gly Ala Pro Gly Pro Ala Gly Pro Pro Gly Ser Arg Gly Asp Pro Gly
1               5                   10                  15
Pro Pro (2) INFORMATION FOR SEQ ID NO:18:

(i) SEQUENCE CHARACTERISTICS:
    (A) LENGTH: 33 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:18:

Gly Ala Pro Gly Ala Pro Gly Ser Gln Gly Ala Pro Gly Leu Gln Gly
1               5                   10                  15
Ala Pro Gly Ala Pro Gly Ser Gln Gly Ala Pro Gly Leu Gln Tyr Met
                20                  25                  30
Lys (2) INFORMATION FOR SEQ ID NO:19:

(i) SEQUENCE CHARACTERISTICS:
    (A) LENGTH: 9 amino acids
    (B) TYPE: amino acid
    (D) TOPOLOGY: linear (ii) MOLECULE TYPE: peptide (xi) SEQUENCE DESCRIPTION: SEQ ID NO:19:

```
        Gly Ala Pro Gly Pro Ala Gly Pro Pro
        1               5
```

( 2 ) INFORMATION FOR SEQ ID NO:20:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

```
        Gly Ser Arg Gly Asp Pro Gly Pro Pro
        1               5
```

( 2 ) INFORMATION FOR SEQ ID NO:21:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

```
        Gly Ala His Gly Pro Ala Gly Pro Lys
        1               5
```

( 2 ) INFORMATION FOR SEQ ID NO:22:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

```
GTGCTGCGGA TGCTCGAGAT GGTGCATGCA TGTACATCCG AGTACTTCGA T            51
```

( 2 ) INFORMATION FOR SEQ ID NO:23:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

```
ATCGAAGTAC TCGGATGTAC ATGCATGCAC CATCTCGAGC ATCCGCA                 47
```

( 2 ) INFORMATION FOR SEQ ID NO:24:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

```
CTACATGTGT TACACATCCC GTGC                                          24
```

( 2 ) INFORMATION FOR SEQ ID NO:25:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

```
GCACGGGATG TGTAACACAT GTAGAGCC                                        28
```

( 2 ) INFORMATION FOR SEQ ID NO:26:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

```
GTGCTCACGG CCCAGCAGGT CCGAAGGGCG CGCATGGCCC AGCAGCCCG AAAGGTGCC        59
```

( 2 ) INFORMATION FOR SEQ ID NO:27:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

```
GCACGGCACC TTTCGGGCCT GCTGGGCCAT GCGCGCCCTT CGGACCTGCT GGGCCGTGA       59
```

( 2 ) INFORMATION FOR SEQ ID NO:28:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:28:

```
GTGCCCATGG CCCAGCAGGA CCGAAAGGAG CTCACGGTCC GGCAGGTCCG AAAG            54
```

( 2 ) INFORMATION FOR SEQ ID NO:29:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

```
GCACCTTTCG GACCTGCCGG ACCGTGAGCT CCTTTCGGTC CTGCTGGGCC ATG             53
```

( 2 ) INFORMATION FOR SEQ ID NO:30:

( i ) SEQUENCE CHARACTERISTICS:
        ( A ) LENGTH: 108 base pairs
        ( B ) TYPE: nucleic acid ( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 1..108

( x i ) SEQUENCE DESCRIPTION: SEQ ID NO:30:

| GGT | GCT | CAC | GGC | CCA | GCA | GGT | CCG | AAG | GGC | GCG | CAT | GGC | CCA | GCA | GGC | 48 |
|-----|-----|-----|-----|-----|-----|-----|-----|-----|-----|-----|-----|-----|-----|-----|-----|----|
| Gly | Ala | His | Gly | Pro | Ala | Gly | Pro | Lys | Gly | Ala | His | Gly | Pro | Ala | Gly | |
| 1 | | | | 5 | | | | | 10 | | | | | 15 | | |

| CCG | AAA | GGT | GCC | CAT | GGC | CCA | GCA | GGA | CCG | AAA | GGA | GCT | CAC | GGT | CCG | 96 |
|-----|-----|-----|-----|-----|-----|-----|-----|-----|-----|-----|-----|-----|-----|-----|-----|----|
| Pro | Lys | Gly | Ala | His | Gly | Pro | Ala | Gly | Pro | Lys | Gly | Ala | His | Gly | Pro | |
| | | 20 | | | | | 25 | | | | | | 30 | | | |

| GCA | GGT | CCG | AAA | 108 |
|-----|-----|-----|-----|-----|
| Ala | Gly | Pro | Lys | |
| | | 35 | | |

( 2 ) INFORMATION FOR SEQ ID NO:31:

( i ) SEQUENCE CHARACTERISTICS:
( A ) LENGTH: 36 amino acids
( B ) TYPE: amino acid
( D ) TOPOLOGY: linear ( i i ) MOLECULE TYPE: protein ( x i ) SEQUENCE DESCRIPTION: SEQ ID NO:31:

| Gly | Ala | His | Gly | Pro | Ala | Gly | Pro | Lys | Gly | Ala | His | Gly | Pro | Ala | Gly |
|-----|-----|-----|-----|-----|-----|-----|-----|-----|-----|-----|-----|-----|-----|-----|-----|
| 1 | | | | 5 | | | | | 10 | | | | | 15 | |

| Pro | Lys | Gly | Ala | His | Gly | Pro | Ala | Gly | Pro | Lys | Gly | Ala | His | Gly | Pro |
|-----|-----|-----|-----|-----|-----|-----|-----|-----|-----|-----|-----|-----|-----|-----|-----|
| | | 20 | | | | | 25 | | | | | | 30 | | |

| Ala | Gly | Pro | Lys |
|-----|-----|-----|-----|
| | | 35 | |

( 2 ) INFORMATION FOR SEQ ID NO:32:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:32:

GTGCGCCTGG ACCGGCTGGT CCACCGGGTG CTCCGGGACC TGCAGGCCCG CCAG     54

( 2 ) INFORMATION FOR SEQ ID NO:33:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:33:

GCACCTGGCG GGCCTGCAGG TCCCGGAGCA CCCGGTGGAC CAGCCGGTCC AGGC     54

( 2 ) INFORMATION FOR SEQ ID NO:34:

( i ) SEQUENCE CHARACTERISTICS:
( A ) LENGTH: 162 base pairs
( B ) TYPE: nucleic acid ( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 1..162

( x i ) SEQUENCE DESCRIPTION: SEQ ID NO:34:

```
GGT GCT CAC GGC CCA GCA GGT CCG AAG GGC GCG CAT GGC CCA GCA GGC    48
Gly Ala His Gly Pro Ala Gly Pro Lys Gly Ala His Gly Pro Ala Gly
 1               5                  10                  15

CCG AAA GGT GCG CCT GGA CCG GCT GGT CCA CCG GGT GCT CCG GGA CCT    96
Pro Lys Gly Ala Pro Gly Pro Ala Gly Pro Pro Gly Ala Pro Gly Pro
             20                  25                  30

GCA GGC CCG CCA GGT GCC CAT GGC CCA GCA GGA CCG AAA GGA GCT CAC   144
Ala Gly Pro Pro Gly Ala His Gly Pro Ala Gly Pro Lys Gly Ala His
         35                  40                  45

GGT CCG GCA GGT CCG AAA                                            162
Gly Pro Ala Gly Pro Lys
 50
```

( 2 ) INFORMATION FOR SEQ ID NO:35:

( i ) SEQUENCE CHARACTERISTICS:
( A ) LENGTH: 54 amino acids
( B ) TYPE: amino acid
( D ) TOPOLOGY: linear ( i i ) MOLECULE TYPE: protein ( x i ) SEQUENCE DESCRIPTION: SEQ ID NO:35:

```
Gly Ala His Gly Pro Ala Gly Pro Lys Gly Ala His Gly Pro Ala Gly
 1               5                  10                  15

Pro Lys Gly Ala Pro Gly Pro Ala Gly Pro Pro Gly Ala Pro Gly Pro
             20                  25                  30

Ala Gly Pro Pro Gly Ala His Gly Pro Ala Gly Pro Lys Gly Ala His
         35                  40                  45

Gly Pro Ala Gly Pro Lys
 50
```

( 2 ) INFORMATION FOR SEQ ID NO:36:

( i ) SEQUENCE CHARACTERISTICS:
( A ) LENGTH: 162 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 1..162

( x i ) SEQUENCE DESCRIPTION: SEQ ID NO:36:

```
GGT GCT CAC GGC CCA GCA GGT CCG AAG GGC GCG CAT GGC CCA GCA GGC    48
Gly Ala His Gly Pro Ala Gly Pro Lys Gly Ala His Gly Pro Ala Gly
 1               5                  10                  15

CCG AAA GGT GCG CCT GGA CCG GCT GGT CCA CCG GGT GCT CCG GGA CCT    96
Pro Lys Gly Ala Pro Gly Pro Ala Gly Pro Pro Gly Ala Pro Gly Pro
             20                  25                  30

GCA GGC CCG CCA GGT GCC CAT GGC CCA GCA GGA CCG AAA GGA GCT CAC   144
Ala Gly Pro Pro Gly Ala His Gly Pro Ala Gly Pro Lys Gly Ala His
         35                  40                  45
```

```
            GGT CCG GCA GGT CCG AAA                                                    162
            Gly Pro Ala Gly Pro Lys
                50
```

( 2 ) INFORMATION FOR SEQ ID NO:37:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: protein ( x i ) SEQUENCE DESCRIPTION: SEQ ID NO:37:

```
Gly Ala His Gly Pro Ala Gly Pro Lys Gly Ala His Gly Pro Ala Gly
 1               5                   10                  15

Pro Lys Gly Ala Pro Gly Pro Ala Gly Pro Pro Gly Ala Pro Gly Pro
            20                  25                  30

Ala Gly Pro Pro Gly Ala His Gly Pro Ala Gly Pro Lys Gly Ala His
            35                  40                  45

Gly Pro Ala Gly Pro Lys
        50
```

( 2 ) INFORMATION FOR SEQ ID NO:38:

( i ) SEQUENCE CHARACTERISTICS:
        ( A ) LENGTH: 84 amino acids
        ( B ) TYPE: amino acid
        ( D ) TOPOLOGY: linear ( i i ) MOLECULE TYPE: protein ( i x ) FEATURE:
        ( A ) NAME/KEY: Duplication
        ( B ) LOCATION: 34..60

( i x ) FEATURE:
        ( A ) NAME/KEY: Duplication
        ( B ) LOCATION: 34..60
        ( D ) OTHER INFORMATION: /label=internalduplica
            / note="34-42 x 2; 43-51 x 24; 52-60 x 2; 34-60 x
            2."

( x i ) SEQUENCE DESCRIPTION: SEQ ID NO:38:

```
Met Asp Pro Val Val Leu Gln Arg Arg Asp Trp Glu Asn Pro Gly Val
 1               5                   10                  15

Thr Gln Leu Asn Arg Leu Ala Ala His Pro Pro Phe Ala Ser Asp Pro
            20                  25                  30

Met Gly Ala His Gly Pro Ala Gly Pro Lys Gly Ala Pro Gly Pro Ala
            35                  40                  45

Gly Pro Pro Gly Ala His Gly Pro Ala Gly Pro Lys Gly Ala Met Asp
        50                  55                  60

Pro Gly Arg Tyr Gln Leu Ser Ala Gly Arg Tyr His Tyr Gln Leu Val
65                  70                  75                  80

Trp Cys Gln Lys
```

( 2 ) INFORMATION FOR SEQ ID NO:39:

( i ) SEQUENCE CHARACTERISTICS:
        ( A ) LENGTH: 84 amino acids
        ( B ) TYPE: amino acid
        ( D ) TOPOLOGY: linear ( i i ) MOLECULE TYPE: protein ( i x ) FEATURE:
        ( A ) NAME/KEY: Duplication (B) LOCATION: 34..60
(D) OTHER INFORMATION: /label=internalduplica
/ note="34-42 x 2; 43-51 x 12; 52-60 x 2; 34-60 x 5."

(xi) SEQUENCE DESCRIPTION: SEQ ID NO:39:

| Met | Asp | Pro | Val | Val | Leu | Gln | Arg | Arg | Asp | Trp | Glu | Asn | Pro | Gly | Val |
|---|---|---|---|---|---|---|---|---|---|---|---|---|---|---|---|
| 1 | | | | 5 | | | | | 10 | | | | | 15 | |

| Thr | Gln | Leu | Asn | Arg | Leu | Ala | Ala | His | Pro | Pro | Phe | Ala | Ser | Asp | Pro |
|---|---|---|---|---|---|---|---|---|---|---|---|---|---|---|---|
| | | | 20 | | | | | 25 | | | | | 30 | | |

| Met | Gly | Ala | His | Gly | Pro | Ala | Gly | Pro | Lys | Gly | Ala | Pro | Gly | Pro | Ala |
|---|---|---|---|---|---|---|---|---|---|---|---|---|---|---|---|
| | | 35 | | | | | 40 | | | | | 45 | | | |

| Gly | Pro | Pro | Gly | Ala | His | Gly | Pro | Ala | Gly | Pro | Lys | Gly | Ala | Met | Asp |
|---|---|---|---|---|---|---|---|---|---|---|---|---|---|---|---|
| | 50 | | | | | 55 | | | | | 60 | | | | |

| Pro | Gly | Arg | Tyr | Gln | Leu | Ser | Ala | Gly | Arg | Tyr | His | Tyr | Gln | Leu | Val |
|---|---|---|---|---|---|---|---|---|---|---|---|---|---|---|---|
| 65 | | | | | 70 | | | | | 75 | | | | | 80 |

Trp Cys Gln Lys (2) INFORMATION FOR SEQ ID NO:40:

(i) SEQUENCE CHARACTERISTICS:
(A) LENGTH: 51 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:40:

GTGCTCCGGG ACCTGCAGAA TATTATTCTA GAGGTGACCC AGGACCGCCT G       51

(2) INFORMATION FOR SEQ ID NO:41:

(i) SEQUENCE CHARACTERISTICS:
(A) LENGTH: 51 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:41:

GCACCACGCG GTCCTGGGTC ACCTCTAGAA TAATATTCTG CAGGTCCCGG A       51

(2) INFORMATION FOR SEQ ID NO:42:

(i) SEQUENCE CHARACTERISTICS:
(A) LENGTH: 67 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:42:

GGCCCACCGG GTAGCCGTGG CGATCCGGGA CCACCGGGTG CACCTGGCCC AGCGGGTCCG       60

CCTGGAT       67

(2) INFORMATION FOR SEQ ID NO:43:

(i) SEQUENCE CHARACTERISTICS:
(A) LENGTH: 75 base pairs
(B) TYPE: nucleic acid
(C) STRANDEDNESS: single
(D) TOPOLOGY: linear ( i i ) MOLECULE TYPE: cDNA ( x i ) SEQUENCE DESCRIPTION: SEQ ID NO:43:

```
CTAGATCCAG GCGGACCCGC TGGGCCAGGT GCACCCGGTG GTCCCGGATC GCCACGGCTA      60
CCCGGTGGGC CTGCA                                                       75
```

( 2 ) INFORMATION FOR SEQ ID NO:44:

( i ) SEQUENCE CHARACTERISTICS:
        ( A ) LENGTH: 108 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..108

( x i ) SEQUENCE DESCRIPTION: SEQ ID NO:44:

```
GGT GCT CCG GGA CCT GCA GGC CCA CCG GGT AGC CGT GGC GAT CCG GGA       48
Gly Ala Pro Gly Pro Ala Gly Pro Pro Gly Ser Arg Gly Asp Pro Gly
 1               5                  10                  15

CCA CCG GGT GCA CCT GGC CCA GCG GGT CCG CCT GGA TCT AGA GGT GAC       96
Pro Pro Gly Ala Pro Gly Pro Ala Gly Pro Pro Gly Ser Arg Gly Asp
                20                  25                  30

CCA GGA CCG CCT                                                      108
Pro Gly Pro Pro
            35
```

( 2 ) INFORMATION FOR SEQ ID NO:45:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: protein ( x i ) SEQUENCE DESCRIPTION: SEQ ID NO:45:

```
Gly Ala Pro Gly Pro Ala Gly Pro Pro Gly Ser Arg Gly Asp Pro Gly
 1               5                  10                  15

Pro Pro Gly Ala Pro Gly Pro Ala Gly Pro Pro Gly Ser Arg Gly Asp
                20                  25                  30

Pro Gly Pro Pro
            35
```

( 2 ) INFORMATION FOR SEQ ID NO:46:

( i ) SEQUENCE CHARACTERISTICS:
        ( A ) LENGTH: 216 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..216

( x i ) SEQUENCE DESCRIPTION: SEQ ID NO:46:

```
GGT GCT CAC GGC CCA GCA GGT CCG AAG GGC GCG CAT GGC CCA GCA GGC       48
Gly Ala His Gly Pro Ala Gly Pro Lys Gly Ala His Gly Pro Ala Gly
 1               5                  10                  15

CCG AAA GGT GCT CCG GGA CCT GCA GGC CCA CCG GGT AGC CGT GGC GAT       96
```

```
Pro Lys Gly Ala Pro Gly Pro Ala Gly Pro Pro Gly Ser Arg Gly Asp
            20                  25                  30

CCG GGA CCA CCG GGT GCA CCT GGC CCA GCG GGT CCG CCT GGA TCT AGA              144
Pro Gly Pro Pro Gly Ala Pro Gly Pro Ala Gly Pro Pro Gly Ser Arg
            35                  40                  45

GGT GAC CCA GGA CCG CCT GGT GCC CAT GGC CCA GCA GGA CCG AAA GGA              192
Gly Asp Pro Gly Pro Pro Gly Ala His Gly Pro Ala Gly Pro Lys Gly
        50                  55                  60

GCT CAC GGT CCG GCA GGT CCG AAA                                              216
Ala His Gly Pro Ala Gly Pro Lys
65                  70
```

( 2 ) INFORMATION FOR SEQ ID NO:47:

( i ) SEQUENCE CHARACTERISTICS:
        ( A ) LENGTH: 72 amino acids
        ( B ) TYPE: amino acid
        ( D ) TOPOLOGY: linear ( i i ) MOLECULE TYPE: protein ( x i ) SEQUENCE DESCRIPTION: SEQ ID NO:47:

```
Gly Ala His Gly Pro Ala Gly Pro Lys Gly Ala His Gly Pro Ala Gly
1               5                   10                  15

Pro Lys Gly Ala Pro Gly Pro Ala Gly Pro Pro Gly Ser Arg Gly Asp
            20                  25                  30

Pro Gly Pro Pro Gly Ala Pro Gly Pro Ala Gly Pro Pro Gly Ser Arg
            35                  40                  45

Gly Asp Pro Gly Pro Pro Gly Ala His Gly Pro Ala Gly Pro Lys Gly
        50                  55                  60

Ala His Gly Pro Ala Gly Pro Lys
65                  70
```

( 2 ) INFORMATION FOR SEQ ID NO:48:

( i ) SEQUENCE CHARACTERISTICS:
        ( A ) LENGTH: 92 amino acids
        ( B ) TYPE: amino acid
        ( D ) TOPOLOGY: linear ( i i ) MOLECULE TYPE: protein ( i x ) FEATURE:
        ( A ) NAME/KEY: Duplication
        ( B ) LOCATION: 34..69
        ( D ) OTHER INFORMATION: /label=internalduplica
            / note="34-42 x 2; 43-60 x 12; 61-69 x 2; 34-69 x
            4."

( x i ) SEQUENCE DESCRIPTION: SEQ ID NO:48:

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala His Gly Pro Ala Gly Pro Lys Gly Ala Pro Gly Pro Ala
            35                  40                  45

Gly Pro Pro Gly Ser Arg Gly Asp Pro Gly Pro Pro Gly Ala His Gly
        50                  55                  60

Pro Ala Gly Pro Lys Gly Ala Met Asp Pro Gly Arg Tyr Gln Leu Ser
65                  70                  75                  80

Ala Gly Arg Tyr His Gln Leu Val Trp Cys Gln Lys
                85                  90
```

(2) INFORMATION FOR SEQ ID NO:49:

(i) SEQUENCE CHARACTERISTICS:
      (A) LENGTH: 9 amino acids
      (B) TYPE: amino acid
      (D) TOPOLOGY: linear (ii) MOLECULE TYPE: peptide (xi) SEQUENCE DESCRIPTION: SEQ ID NO:49:

Gly Ser Arg Gly Asp Pro Gly Pro Pro
   1               5

(2) INFORMATION FOR SEQ ID NO:50:

(i) SEQUENCE CHARACTERISTICS:
      (A) LENGTH: 9 amino acids
      (B) TYPE: amino acid
      (D) TOPOLOGY: linear (ii) MOLECULE TYPE: peptide (xi) SEQUENCE DESCRIPTION: SEQ ID NO:50:

Gly Ala His Gly Pro Ala Gly Pro Lys
   1               5

(2) INFORMATION FOR SEQ ID NO:51:

(i) SEQUENCE CHARACTERISTICS:
      (A) LENGTH: 9 amino acids
      (B) TYPE: amino acid
      (D) TOPOLOGY: linear (ii) MOLECULE TYPE: peptide (xi) SEQUENCE DESCRIPTION: SEQ ID NO:51:

Gly Ala Gln Gly Pro Ala Gly Pro Gly
   1               5

(2) INFORMATION FOR SEQ ID NO:52:

(i) SEQUENCE CHARACTERISTICS:
      (A) LENGTH: 54 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:52:

GTGCACAGGG ACCGGCGGGA CCAGGTGGCT CTCGAGGCGA TCCGGGTCCT CCGG          54

(2) INFORMATION FOR SEQ ID NO:53:

(i) SEQUENCE CHARACTERISTICS:
      (A) LENGTH: 54 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:53:

GCACCCGGAG GACCCGGATC GCCTCGAGAG CCACCTGGTC CCGCCGGTCC CTGT          54

(2) INFORMATION FOR SEQ ID NO:54:

(i) SEQUENCE CHARACTERISTICS:
      (A) LENGTH: 54 base pairs
      (B) TYPE: nucleic acid (C) STRANDEDNESS: single
(D) TOPOLOGY: linear (ii) MOLECULE TYPE: cDNA (xi) SEQUENCE DESCRIPTION: SEQ ID NO:54:

GTGCACAAGG ACCGGCAGGC CTGGTGGCA GCCGCGGTGA TCCGGGCCCA CCGG    54

(2) INFORMATION FOR SEQ ID NO:55:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:55:

GCACCCGGTG GGCCCGGATC ACCGCGGCTG CCACCAGGGC CTGCCGGTCC TTGT    54

(2) INFORMATION FOR SEQ ID NO:56:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:56:

GTGCTCAAGG ACCGGCTGGC CCAGGCGGTT CCCGTGGAGA CCCGGGTCCA CCGG    54

(2) INFORMATION FOR SEQ ID NO:57:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:57:

GCACCCGGTG GACCCGGGTC TCCACGGGAA CCGCCTGGGC CAGCCGGTCC TTGA    54

(2) INFORMATION FOR SEQ ID NO:58:

(i) SEQUENCE CHARACTERISTICS:
(A) LENGTH: 162 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 1..162

(xi) SEQUENCE DESCRIPTION: SEQ ID NO:58:

```
GGT GCA CAG GGA CCG GCG GGA CCA GGT GGC TCT CGA GGC GAT CCG GGT       48
Gly Ala Gln Gly Pro Ala Gly Pro Gly Gly Ser Arg Gly Asp Pro Gly
 1               5                  10                  15

CCT CCG GGT GCA CAA GGA CCG GCA GGC CCT GGT GGC AGC CGC GGT GAT       96
Pro Pro Gly Ala Gln Gly Pro Ala Gly Pro Gly Gly Ser Arg Gly Asp
                 20                  25                  30

CCG GGC CCA CCG GGT GCT CAA GGA CCG GCT GGC CCA GGC GGT TCC CGT      144
```

```
                                                             5,496,712
                          61                                                           62
                                                       -continued Pro  Gly  Pro  Pro  Gly  Ala  Gln  Gly  Pro  Ala  Gly  Pro  Gly  Gly  Ser  Arg
          35                      40                      45

GGA  GAC  CCG  GGT  CCA  CCG                                                                           162
Gly  Asp  Pro  Gly  Pro  Pro
          50
```

( 2 ) INFORMATION FOR SEQ ID NO:59:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: protein ( x i ) SEQUENCE DESCRIPTION: SEQ ID NO:59:

```
Gly  Ala  Gln  Gly  Pro  Ala  Gly  Pro  Gly  Gly  Ser  Arg  Gly  Asp  Pro  Gly
1                   5                        10                      15

Pro  Pro  Gly  Ala  Gln  Gly  Pro  Ala  Gly  Pro  Gly  Gly  Ser  Arg  Gly  Asp
               20                      25                      30

Pro  Gly  Pro  Pro  Gly  Ala  Gln  Gly  Pro  Ala  Gly  Pro  Gly  Gly  Ser  Arg
          35                      40                      45

Gly  Asp  Pro  Gly  Pro  Pro
          50
```

( 2 ) INFORMATION FOR SEQ ID NO:60:

( i ) SEQUENCE CHARACTERISTICS:
        ( A ) LENGTH: 93 amino acids
        ( B ) TYPE: amino acid
        ( D ) TOPOLOGY: linear ( i i ) MOLECULE TYPE: protein ( i x ) FEATURE:
        ( A ) NAME/KEY: Duplication
        ( B ) LOCATION: 34..69
        ( D ) OTHER INFORMATION: /label=internalduplica
            / note="34-42 x 2; 43-60 x 12; 61-69 x 2; 34-69 x
            4."

( x i ) SEQUENCE DESCRIPTION: SEQ ID NO:60:

```
Met  Asp  Pro  Val  Val  Leu  Gln  Arg  Arg  Asp  Trp  Glu  Asn  Pro  Gly  Val
1                   5                        10                      15

Thr  Gln  Leu  Asn  Arg  Leu  Ala  Ala  His  Pro  Pro  Phe  Ala  Ser  Asp  Pro
               20                      25                      30

Met  Gly  Ala  His  Gly  Pro  Ala  Gly  Pro  Lys  Gly  Ala  Gln  Gly  Pro  Ala
          35                      40                      45

Gly  Pro  Gly  Gly  Ser  Arg  Gly  Asp  Pro  Gly  Pro  Pro  Gly  Ala  His  Gly
     50                      55                      60

Pro  Ala  Gly  Pro  Lys  Gly  Ala  Met  Asp  Pro  Gly  Arg  Tyr  Gln  Leu  Ser
65                       70                      75                            80

Ala  Gly  Arg  Tyr  His  Tyr  Gln  Leu  Val  Trp  Cys  Cys  Lys
                    85                      90
```

( 2 ) INFORMATION FOR SEQ ID NO:61:

( i ) SEQUENCE CHARACTERISTICS:
        ( A ) LENGTH: 93 amino acids
        ( B ) TYPE: amino acid
        ( D ) TOPOLOGY: linear ( i i ) MOLECULE TYPE: protein ( i x ) FEATURE:
        ( A ) NAME/KEY: Duplication (B) LOCATION: 34..69
(D) OTHER INFORMATION: /label=internalduplica
/ note="34-42 x 2; 43-60 x 6; 61-69 x 2; 34-69 x 4."

(xi) SEQUENCE DESCRIPTION: SEQ ID NO:61:

| Met | Asp | Pro | Val | Val | Leu | Gln | Arg | Arg | Asp | Trp | Glu | Asn | Pro | Gly | Val |
| 1 | | | | 5 | | | | | 10 | | | | | 15 | |
| Thr | Gln | Leu | Asn | Arg | Leu | Ala | Ala | His | Pro | Pro | Phe | Ala | Ser | Asp | Pro |
| | | | 20 | | | | | 25 | | | | | 30 | | |
| Met | Gly | Ala | His | Gly | Pro | Ala | Gly | Pro | Lys | Gly | Ala | Gln | Gly | Pro | Ala |
| | | 35 | | | | | 40 | | | | | 45 | | | |
| Gly | Pro | Gly | Gly | Ser | Arg | Gly | Asp | Pro | Gly | Pro | Pro | Gly | Ala | His | Gly |
| | 50 | | | | | 55 | | | | | 60 | | | | |
| Pro | Ala | Gly | Pro | Lys | Gly | Ala | Met | Asp | Pro | Gly | Arg | Tyr | Gln | Leu | Ser |
| 65 | | | | 70 | | | | | 75 | | | | | 80 | |
| Ala | Gly | Arg | Tyr | His | Tyr | Gln | Leu | Val | Trp | Cys | Gln | Lys |
| | | | | 85 | | | | 90 | | | | |

(2) INFORMATION FOR SEQ ID NO:62:

(i) SEQUENCE CHARACTERISTICS:
(A) LENGTH: 58 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:62:

GTGCACAGGG ACCGGCGGGT CCAGGCGGTG CTCAAGGACC GGCAGGCCCT TAATTAAG  58

(2) INFORMATION FOR SEQ ID NO:63:

(i) SEQUENCE CHARACTERISTICS:
(A) LENGTH: 58 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:63:

GCACCTTAAT TAAGGGCCTG CCGGTCCTTG AGCACCGCCT GGACCCGCCG GTCCCTGT  58

(2) INFORMATION FOR SEQ ID NO:64:

(i) SEQUENCE CHARACTERISTICS:
(A) LENGTH: 63 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:64:

GCCCTGGTGG CGCTCAAGGT CCGGCTGGCC CAGGAGGCGC GCAGGGTCCG GCAGGTCCGG  60

GAG  63

(2) INFORMATION FOR SEQ ID NO:65:

(i) SEQUENCE CHARACTERISTICS:
(A) LENGTH: 64 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:65:

```
GCACCTCCCG GACCTGCCGG ACCCTGCGCG CCTCCTGGGC CAGCCGGACC TTGAGCGCCA        60

CCAG                                                                     64
```

(2) INFORMATION FOR SEQ ID NO:66:

(i) SEQUENCE CHARACTERISTICS:
        (A) LENGTH: 108 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..108

(xi) SEQUENCE DESCRIPTION: SEQ ID NO:66:

```
GGT GCA CAG GGA CCG GCG GGT CCA GGC GGT GCT CAA GGA CCG GCA GGC           48
Gly Ala Gln Gly Pro Ala Gly Pro Gly Gly Ala Gln Gly Pro Ala Gly
 1               5                  10                  15

CCT GGT GGC GCT CAA GGT CCG GCT GGC CCA GGA GGC GCG CAG GGT CCG           96
Pro Gly Gly Ala Gln Gly Pro Ala Gly Pro Gly Gly Ala Gln Gly Pro
             20                  25                  30

GCA GGT CCG GGA                                                          108
Ala Gly Pro Gly
         35
```

(2) INFORMATION FOR SEQ ID NO:67:

(i) SEQUENCE CHARACTERISTICS:
        (A) LENGTH: 36 amino acids
        (B) TYPE: amino acid
        (D) TOPOLOGY: linear (ii) MOLECULE TYPE: protein (xi) SEQUENCE DESCRIPTION: SEQ ID NO:67:

```
Gly Ala Gln Gly Pro Ala Gly Pro Gly Gly Ala Gln Gly Pro Ala Gly
 1               5                  10                  15

Pro Gly Gly Ala Gln Gly Pro Ala Gly Pro Gly Gly Ala Gln Gly Pro
             20                  25                  30

Ala Gly Pro Gly
         35
```

(2) INFORMATION FOR SEQ ID NO:68:

(i) SEQUENCE CHARACTERISTICS:
        (A) LENGTH: 84 amino acids
        (B) TYPE: amino acid
        (D) TOPOLOGY: linear (ii) MOLECULE TYPE: protein (ix) FEATURE:
        (A) NAME/KEY: Duplication
        (B) LOCATION: 34..60
        (D) OTHER INFORMATION: /label=internalduplica
            / note="34-42 x 2; 43-51 x 24; 52-60 x 2; 34-60 x
            4."

(xi) SEQUENCE DESCRIPTION: SEQ ID NO:68:

```
Met Asp Pro Val Val Leu Gln Arg Arg Asp Trp Glu Asn Pro Gly Val
 1               5                  10                  15
```

```
        Thr   Gln   Leu   Asn   Arg   Leu   Ala   Ala   His   Pro   Pro   Phe   Ala   Ser   Asp   Pro
                          20                        25                        30

Met   Gly   Ala   His   Gly   Pro   Ala   Gly   Pro   Lys   Gly   Ala   Gln   Gly   Pro   Ala
                    35                        40                        45

Gly   Pro   Gly   Gly   Ala   His   Gly   Pro   Ala   Gly   Pro   Lys   Gly   Ala   Met   Asp
              50                        55                        60

Pro   Gly   Arg   Tyr   Gln   Leu   Ser   Ala   Gly   Arg   Tyr   His   Tyr   Gln   Leu   Val
        65                        70                        75                              80

Trp   Cys   Cys   Lys
```

( 2 ) INFORMATION FOR SEQ ID NO:69:

( i ) SEQUENCE CHARACTERISTICS:
        ( A ) LENGTH: 63 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:69:

```
GCTATGTTTA  AACCACGTGT  TCGCGATCCG  GGTGCCGATC  CAGGCCTGCG  ATATCAGTAC      60
GTA                                                                         63
```

( 2 ) INFORMATION FOR SEQ ID NO:70:

( i ) SEQUENCE CHARACTERISTICS:
        ( A ) LENGTH: 62 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: misc_binding
        ( B ) LOCATION: 5..62
        ( D ) OTHER INFORMATION: /note="Bound to SEQ ID NO:71
            between base numbers 5 and 62."

( x i ) SEQUENCE DESCRIPTION: SEQ ID NO:70:

```
GTGCCCCTGG  CGCTCCGGGT  TCTCAAGGTG  CACCGGGTCT  GCAGAAAGGG  CTCTTTCACC      60
GG                                                                          62
```

( 2 ) INFORMATION FOR SEQ ID NO:71:

( i ) SEQUENCE CHARACTERISTICS:
        ( A ) LENGTH: 62 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: misc_binding
        ( B ) LOCATION: 5..62
        ( D ) OTHER INFORMATION: /note="Bound to SEQ ID No:70
            between base numbers 5 and 62."

( x i ) SEQUENCE DESCRIPTION: SEQ ID NO:71:

```
GCACCCGGTG  AAAGAGCCCT  TTCTGCAGAC  CCGGTGCACC  TTGAGAACCC  GGAGCGCCAG      60
GG                                                                          62
```

( 2 ) INFORMATION FOR SEQ ID NO:72:

( i ) SEQUENCE CHARACTERISTICS:
    ( A ) LENGTH: 52 base pairs
    ( B ) TYPE: nucleic acid
    ( C ) STRANDEDNESS: both
    ( D ) TOPOLOGY: linear ( i i ) MOLECULE TYPE: cDNA ( i x ) FEATURE:
    ( A ) NAME/KEY: misc_binding
    ( B ) LOCATION: 1..48
    ( D ) OTHER INFORMATION: /note="Bound to SEQ ID NO:73
        between base numbers 5 and 48."

( x i ) SEQUENCE DESCRIPTION: SEQ ID NO:72:

GGGTGCACCG GGAGCGCCAG GTAGCCAGGG TGCACCGGGA TTGCAGGGGG CT        52

( 2 ) INFORMATION FOR SEQ ID NO:73:

( i ) SEQUENCE CHARACTERISTICS:
    ( A ) LENGTH: 52 base pairs
    ( B ) TYPE: nucleic acid
    ( C ) STRANDEDNESS: both
    ( D ) TOPOLOGY: linear ( i i ) MOLECULE TYPE: cDNA ( i x ) FEATURE:
    ( A ) NAME/KEY: misc_binding
    ( B ) LOCATION: 1..48
    ( D ) OTHER INFORMATION: /note="Bound to SEQ ID NO:72
        between base numbers 1 and 48."

( x i ) SEQUENCE DESCRIPTION: SEQ ID NO:73:

CCCTGCAATC CCGGTGCACC CTGGCTACCT GGCGCTCCCG GTGCACCCTG CA        52

( 2 ) INFORMATION FOR SEQ ID NO:74:

( i ) SEQUENCE CHARACTERISTICS:
    ( A ) LENGTH: 49 base pairs
    ( B ) TYPE: nucleic acid
    ( C ) STRANDEDNESS: both
    ( D ) TOPOLOGY: linear ( i i ) MOLECULE TYPE: cDNA ( i x ) FEATURE:
    ( A ) NAME/KEY: misc_binding
    ( B ) LOCATION: 1..46
    ( D ) OTHER INFORMATION: /note="Bound to SEQ ID NO:75
        between base numbers 1 and 46."

( x i ) SEQUENCE DESCRIPTION: SEQ ID NO:74:

CCGGGTGCAC CAGGTAGCCA GGGAGCACCG GGTCTGCAAG GAGCACCGG            49

( 2 ) INFORMATION FOR SEQ ID NO:75:

( i ) SEQUENCE CHARACTERISTICS:
    ( A ) LENGTH: 50 base pairs
    ( B ) TYPE: nucleic acid
    ( C ) STRANDEDNESS: both
    ( D ) TOPOLOGY: linear ( i i ) MOLECULE TYPE: cDNA ( i x ) FEATURE:
    ( A ) NAME/KEY: misc_binding
    ( B ) LOCATION: 1..46
    ( D ) OTHER INFORMATION: /note="Bound to SEQ ID NO:74
        between base numbers 1-46."

( x i ) SEQUENCE DESCRIPTION: SEQ ID NO:75:

GTGCTCCTTG CAGACCGCCT GCTCCCTGGC TACCTGGTGC ACCCGGAGCC        50

( 2 ) INFORMATION FOR SEQ ID NO:76:

( i ) SEQUENCE CHARACTERISTICS:
    ( A ) LENGTH: 55 base pairs
    ( B ) TYPE: nucleic acid
    ( C ) STRANDEDNESS: both
    ( D ) TOPOLOGY: linear ( i i ) MOLECULE TYPE: cDNA ( i x ) FEATURE:
    ( A ) NAME/KEY: misc_binding
    ( B ) LOCATION: 1..55
    ( D ) OTHER INFORMATION: /note="Bound to SEQ ID NO:77
      between base numbers 1-55."

( x i ) SEQUENCE DESCRIPTION: SEQ ID NO:76:

GTGCACCGGG ATCCCAGGGC GCTCCGGGCC TGCAAGGTGC CATGGACCCT GAAGT        55

( 2 ) INFORMATION FOR SEQ ID NO:77:

( i ) SEQUENCE CHARACTERISTICS:
    ( A ) LENGTH: 58 base pairs
    ( B ) TYPE: nucleic acid
    ( C ) STRANDEDNESS: both
    ( D ) TOPOLOGY: linear ( i i ) MOLECULE TYPE: cDNA ( i x ) FEATURE:
    ( A ) NAME/KEY: misc_binding
    ( B ) LOCATION: 1..55
    ( D ) OTHER INFORMATION: /note="Bound to SEQ ID NO:76
      between base numbers 1 and 55."

( x i ) SEQUENCE DESCRIPTION: SEQ ID NO:77:

ACTTCAGGGT CCATGGCACC TTGCAGGCCC GGACGGCCCT GGGATCCCGG TGCACCCG        58

( 2 ) INFORMATION FOR SEQ ID NO:78:

( i ) SEQUENCE CHARACTERISTICS:
    ( A ) LENGTH: 169 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: join(1..129, 131..163)

( x i ) SEQUENCE DESCRIPTION: SEQ ID NO:78:

```
GGT GCC CCT GGC GCT CCG GGT TCT CAA GGT GCA CCG GGT CTG CAG GGT          48
Gly Ala Pro Gly Ala Pro Gly Ser Gln Gly Ala Pro Gly Leu Gln Gly
 1               5                  10                  15

GCA CCG GGA GCG CCA GGT AGC CAG GGT GCA CCG GGA TTG CAG GGG GCT          96
Ala Pro Gly Ala Pro Gly Ser Gln Gly Ala Pro Gly Leu Gln Gly Ala
             20                  25                  30

CCG GGT GCA CCA GGT AGC CAG GGA GCA CCG GGT T GCA CCG GGA TCC           142
Pro Gly Ala Pro Gly Ser Gln Gly Ala Pro Gly   Ala Pro Gly Ser
         35                  40                      45

CAG GGC GCT CCG GGC CTG CAA GGTGCC                                      169
Gln Gly Ala Pro Gly Leu Gln
         50
```

( 2 ) INFORMATION FOR SEQ ID NO:79:

( i ) SEQUENCE CHARACTERISTICS:
  ( A ) LENGTH: 54 amino acids
  ( B ) TYPE: amino acid
  ( D ) TOPOLOGY: linear ( i i ) MOLECULE TYPE: protein ( x i ) SEQUENCE DESCRIPTION: SEQ ID NO:79:

```
Gly Ala Pro Gly Ala Pro Gly Ser Gln Gly Ala Pro Gly Leu Gln Gly
  1               5                  10                  15

Ala Pro Gly Ala Pro Gly Ser Gln Gly Ala Pro Gly Leu Gln Gly Ala
                 20                  25                  30

Pro Gly Ala Pro Gly Ser Gln Gly Ala Pro Gly Ala Pro Gly Ser Gln
             35                  40                  45

Gly Ala Pro Gly Leu Gln
             50
```

( 2 ) INFORMATION FOR SEQ ID NO:80:

( i ) SEQUENCE CHARACTERISTICS:
    ( A ) LENGTH: 186 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: 1..180

( x i ) SEQUENCE DESCRIPTION: SEQ ID NO:80:

```
GGT GCC CCT GGC GCT CCG GGT TCT CAA GGT GCA CCG GGT CTG CAG GGT     48
Gly Ala Pro Gly Ala Pro Gly Ser Gln Gly Ala Pro Gly Leu Gln Gly
  1               5                  10                  15

GCA CCG GGA GCG CCA GGT AGC CAG GGT GCA CCG GGA TTG CAG GGG GCT     96
Ala Pro Gly Ala Pro Gly Ser Gln Gly Ala Pro Gly Leu Gln Gly Ala
                 20                  25                  30

CCG GGT GCA CCA GGT AGC CAG GGA GCA CCG GGT CTG CAA GGA GCA CCG    144
Pro Gly Ala Pro Gly Ser Gln Gly Ala Pro Gly Leu Gln Gly Ala Pro
             35                  40                  45

GGT GCA CCG GGA TCC CAG GGC GCT CCG GGC CTG CAA GGTGCC             186
Gly Ala Pro Gly Ser Gln Gly Ala Pro Gly Leu Gln
             50                  55                  60
```

( 2 ) INFORMATION FOR SEQ ID NO:81:

( i ) SEQUENCE CHARACTERISTICS:
    ( A ) LENGTH: 60 amino acids
    ( B ) TYPE: amino acid
    ( D ) TOPOLOGY: linear ( i i ) MOLECULE TYPE: protein ( x i ) SEQUENCE DESCRIPTION: SEQ ID NO:81:

```
Gly Ala Pro Gly Ala Pro Gly Ser Gln Gly Ala Pro Gly Leu Gln Gly
  1               5                  10                  15

Ala Pro Gly Ala Pro Gly Ser Gln Gly Ala Pro Gly Leu Gln Gly Ala
                 20                  25                  30

Pro Gly Ala Pro Gly Ser Gln Gly Ala Pro Gly Leu Gln Gly Ala Pro
             35                  40                  45

Gly Ala Pro Gly Ser Gln Gly Ala Pro Gly Leu Gln
             50                  55                  60
```

( 2 ) INFORMATION FOR SEQ ID NO:82:

( i ) SEQUENCE CHARACTERISTICS:
  ( A ) LENGTH: 1077 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:82:

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Pro Gly Ala Pro Gly Ser Gln Gly Ala Pro Gly Leu Gln
        35                  40                  45

Gly Ala Pro Gly Ala Pro Gly Ser Gln Gly Ala Pro Gly Leu Gln Gly
    50                  55                  60

Ala Pro Gly Ala Pro Gly Ser Gln Gly Ala Pro Gly Leu Gln Gly Ala
65                  70                  75                  80

Pro Gly Ala Pro Gly Ser Gln Gly Ala Pro Gly Leu Gln Gly Ala Pro
                85                  90                  95

Gly Ala Pro Gly Ser Gln Gly Ala Pro Gly Leu Gln Gly Ala Pro Gly
            100                 105                 110

Ala Pro Gly Ser Gln Gly Ala Pro Gly Leu Gln Gly Ala Pro Gly Ala
        115                 120                 125

Pro Gly Ser Gln Gly Ala Pro Gly Leu Gln Gly Ala Pro Gly Ala Pro
    130                 135                 140

Gly Ser Gln Gly Ala Pro Gly Leu Gln Gly Ala Pro Gly Ala Pro Gly
145                 150                 155                 160

Ser Gln Gly Ala Pro Gly Leu Gln Gly Ala Pro Gly Ala Pro Gly Ser
                165                 170                 175

Gln Gly Ala Pro Gly Leu Gln Gly Ala Pro Gly Ala Pro Gly Ser Gln
            180                 185                 190

Gly Ala Pro Gly Leu Gln Gly Ala Pro Gly Ala Pro Gly Ser Gln Gly
        195                 200                 205

Ala Pro Gly Leu Gln Gly Ala Pro Gly Ala Pro Gly Ser Gln Gly Ala
    210                 215                 220

Pro Gly Leu Gln Gly Ala Pro Gly Ala Pro Gly Ser Gln Gly Ala Pro
225                 230                 235                 240

Gly Leu Gln Gly Ala Pro Gly Ala Pro Gly Ser Gln Gly Ala Pro Gly
                245                 250                 255

Leu Gln Gly Ala Pro Gly Ala Pro Gly Ser Gln Gly Ala Pro Gly Leu
            260                 265                 270

Gln Gly Ala Pro Gly Ala Pro Gly Ser Gln Gly Ala Pro Gly Leu Gln
        275                 280                 285

Gly Ala Pro Gly Ala Pro Gly Ser Gln Gly Ala Pro Gly Leu Gln Gly
    290                 295                 300

Ala Pro Gly Ala Pro Gly Ser Gln Gly Ala Pro Gly Leu Gln Gly Ala
305                 310                 315                 320

Pro Gly Ala Pro Gly Ser Gln Gly Ala Pro Gly Leu Gln Gly Ala Pro
                325                 330                 335

Gly Ala Pro Gly Ser Gln Gly Ala Pro Gly Leu Gln Gly Ala Pro Gly
            340                 345                 350

Ala Pro Gly Ser Gln Gly Ala Pro Gly Leu Gln Gly Ala Pro Gly Ala
        355                 360                 365
```

```
Pro  Gly  Ser  Gln  Gly  Ala  Pro  Gly  Leu  Gln  Gly  Ala  Pro  Gly  Ala  Pro
     370                 375                 380

Gly  Ser  Gln  Gly  Ala  Pro  Gly  Leu  Gln  Gly  Ala  Pro  Gly  Ala  Pro  Gly
385                      390                 395                           400

Ser  Gln  Gly  Ala  Pro  Gly  Leu  Gln  Gly  Ala  Pro  Gly  Ala  Pro  Gly  Ser
                    405                 410                      415

Gln  Gly  Ala  Pro  Gly  Leu  Gln  Gly  Ala  Pro  Gly  Ala  Pro  Gly  Ser  Gln
               420                 425                      430

Gly  Ala  Pro  Gly  Leu  Gln  Gly  Ala  Pro  Gly  Ala  Pro  Gly  Ser  Gln  Gly
          435                 440                      445

Ala  Pro  Gly  Leu  Gln  Gly  Ala  Pro  Gly  Ala  Pro  Gly  Ser  Gln  Gly  Ala
     450                 455                      460

Pro  Gly  Leu  Gln  Gly  Ala  Pro  Gly  Ala  Pro  Gly  Ser  Gln  Gly  Ala  Pro
465                 470                      475                           480

Gly  Leu  Gln  Gly  Ala  Pro  Gly  Ala  Pro  Gly  Ser  Gln  Gly  Ala  Pro  Gly
               485                      490                      495

Leu  Gln  Gly  Ala  Pro  Gly  Ala  Pro  Gly  Ser  Gln  Gly  Ala  Pro  Gly  Leu
               500                 505                      510

Gln  Gly  Ala  Pro  Gly  Ala  Pro  Gly  Ser  Gln  Gly  Ala  Pro  Gly  Leu  Gln
          515                 520                      525

Gly  Ala  Pro  Gly  Ala  Pro  Gly  Ser  Gln  Gly  Ala  Pro  Gly  Leu  Gln  Gly
     530                 535                      540

Ala  Pro  Gly  Ala  Pro  Gly  Ser  Gln  Gly  Ala  Pro  Gly  Leu  Gln  Gly  Ala
545                 550                      555                           560

Pro  Gly  Ala  Pro  Gly  Ser  Gln  Gly  Ala  Pro  Gly  Leu  Gln  Gly  Ala  Pro
               565                 570                      575

Gly  Ala  Pro  Gly  Ser  Gln  Gly  Ala  Pro  Gly  Leu  Gln  Gly  Ala  Pro  Gly
          580                 585                      590

Ala  Pro  Gly  Ser  Gln  Gly  Ala  Pro  Gly  Leu  Gln  Gly  Ala  Pro  Gly  Ala
     595                 600                      605

Pro  Gly  Ser  Gln  Gly  Ala  Pro  Gly  Leu  Gln  Gly  Ala  Pro  Gly  Ala  Pro
610                 615                      620

Gly  Ser  Gln  Gly  Ala  Pro  Gly  Leu  Gln  Gly  Ala  Pro  Gly  Ala  Pro  Gly
625                 630                      635                           640

Ser  Gln  Gly  Ala  Pro  Gly  Leu  Gln  Gly  Ala  Pro  Gly  Ala  Pro  Gly  Ser
               645                 650                      655

Gln  Gly  Ala  Pro  Gly  Leu  Gln  Gly  Ala  Pro  Gly  Ala  Pro  Gly  Ser  Gln
          660                 665                      670

Gly  Ala  Pro  Gly  Leu  Gln  Gly  Ala  Pro  Gly  Ala  Pro  Gly  Ser  Gln  Gly
     675                 680                      685

Ala  Pro  Gly  Leu  Gln  Gly  Ala  Pro  Gly  Ala  Pro  Gly  Ser  Gln  Gly  Ala
690                 695                      700

Pro  Gly  Leu  Gln  Gly  Ala  Pro  Gly  Ala  Pro  Gly  Ser  Gln  Gly  Ala  Pro
705                 710                      715                           720

Gly  Leu  Gln  Gly  Ala  Pro  Gly  Ala  Pro  Gly  Ser  Gln  Gly  Ala  Pro  Gly
               725                      730                      735

Leu  Gln  Gly  Ala  Pro  Gly  Ala  Pro  Gly  Ser  Gln  Gly  Ala  Pro  Gly  Leu
               740                 745                      750

Gln  Gly  Ala  Pro  Gly  Ala  Pro  Gly  Ser  Gln  Gly  Ala  Pro  Gly  Leu  Gln
          755                 760                      765

Gly  Ala  Pro  Gly  Ala  Pro  Gly  Ser  Gln  Gly  Ala  Pro  Gly  Leu  Gln  Gly
     770                 775                      780

Ala  Pro  Gly  Ala  Pro  Gly  Ser  Gln  Gly  Ala  Pro  Gly  Leu  Gln  Gly  Ala
785                 790                      795                           800
```

Pro Gly Ala Pro Gly Ser Gln Gly Ala Pro Gly Leu Gln Gly Ala Pro
                    805                 810                 815
Gly Ala Pro Gly Ser Gln Gly Ala Pro Gly Leu Gln Gly Ala Pro Gly
            820                 825                 830
Ala Pro Gly Ser Gln Gly Ala Pro Gly Leu Gln Gly Ala Pro Gly Ala
        835                 840                 845
Pro Gly Ser Gln Gly Ala Pro Gly Leu Gln Gly Ala Pro Gly Ala Pro
    850                 855                 860
Gly Ser Gln Gly Ala Pro Gly Leu Gln Gly Ala Pro Gly Ala Pro Gly
865                 870                 875                 880
Ser Gln Gly Ala Pro Gly Leu Gln Gly Ala Pro Gly Ala Pro Gly Ser
                885                 890                 895
Gln Gly Ala Pro Gly Leu Gln Gly Ala Pro Gly Ala Pro Gly Ser Gln
            900                 905                 910
Gly Ala Pro Gly Leu Gln Gly Ala Pro Gly Ala Pro Gly Ser Gln Gly
        915                 920                 925
Ala Pro Gly Leu Gln Gly Ala Pro Gly Ala Pro Gly Ser Gln Gly Ala
    930                 935                 940
Pro Gly Leu Gln Gly Ala Pro Gly Ala Pro Gly Ser Gln Gly Ala Pro
945                 950                 955                 960
Gly Leu Gln Gly Ala Pro Gly Ala Pro Gly Ser Gln Gly Ala Pro Gly
                965                 970                 975
Leu Gln Gly Ala Pro Gly Ala Pro Gly Ser Gln Gly Ala Pro Gly Leu
            980                 985                 990
Gln Gly Ala Pro Gly Ala Pro Gly Ser Gln Gly Ala Pro Gly Leu Gln
        995                 1000                1005
Gly Ala Pro Gly Ala Pro Gly Ser Gln Gly Ala Pro Gly Leu Gln Gly
    1010                1015                1020
Ala Pro Gly Ala Pro Gly Ser Gln Gly Ala Pro Gly Leu Gln Gly Ala
1025                1030                1035                1040
Pro Gly Ala Pro Gly Ser Gln Gly Ala Pro Gly Leu Gln Gly Ala Met
                1045                1050                1055
Asp Pro Gly Arg Tyr Gln Leu Ser Ala Gly Arg Tyr His Tyr Gln Leu
            1060                1065                1070
Trp Val Cys Gln Lys
        1075

( 2 ) INFORMATION FOR SEQ ID NO:83:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:83:

Gly Ala Pro Gly Pro Ala Gly Pro Pro Gly Ser Arg Gly Asp Pro Gly
1               5                   10                  15
Pro Pro ( 2 ) INFORMATION FOR SEQ ID NO:84:

( i ) SEQUENCE CHARACTERISTICS:
        ( A ) LENGTH: 18 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:84:

Gly Ala Gln Gly Pro Ala Gly Pro Gly Gly Ser Arg Gly Asp Pro Gly
1               5                   10                  15
Pro Pro (2) INFORMATION FOR SEQ ID NO:85:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:85:

Gly Ala Gln Gly Pro Ala Gly Pro Gly
1               5